(12) United States Patent
Van Berkel et al.

(10) Patent No.: US 7,060,677 B1
(45) Date of Patent: Jun. 13, 2006

(54) ANTIMICROBIAL ACTIVITY OF THE FIRST CATIONIC CLUSTER OF HUMAN LACTOFERRIN

(75) Inventors: Patrick H. C. Van Berkel, Berkel en Rodenrijs (NL); Peter Hendikus Nibbering, Voorhout (NL); Jan Henricus Nuijens, Heiloo (NL)

(73) Assignee: AM-Pharma B.V. (NL)

( * ) Notice: Subject to any disclaimer, the term of this patent is extended or adjusted under 35 U.S.C. 154(b) by 315 days.

(21) Appl. No.: 10/130,180

(22) PCT Filed: Nov. 10, 2000

(86) PCT No.: PCT/NL00/00821

§ 371 (c)(1),
(2), (4) Date: May 10, 2002

(87) PCT Pub. No.: WO01/34641

PCT Pub. Date: May 17, 2001

Related U.S. Application Data

(60) Provisional application No. 60/164,975, filed on Nov. 11, 1999.

(30) Foreign Application Priority Data

Nov. 11, 1999 (EP) .................................. 99203775

(51) Int. Cl.
*A61K 38/00* (2006.01)
(52) U.S. Cl. ............................................ 514/6; 514/12
(58) Field of Classification Search ............ 514/2, 514/6, 12
See application file for complete search history.

(56) References Cited

U.S. PATENT DOCUMENTS 5,304,633 A  4/1994 Tomita et al.
5,861,491 A  1/1999 Nuijens et al.
6,333,311 B1 * 12/2001 Nuijens et al. ................ 514/12

FOREIGN PATENT DOCUMENTS

| EP | 0 629 347 A1 | 12/1994 |
|---|---|---|
| JP | 8073499 | 3/1996 |
| JP | 11-92375/1999 A | 4/1999 |
| JP | 11092375 | 4/1999 |
| WO | WO 00/49040 A2 | 8/2000 |

OTHER PUBLICATIONS

Ellison et al., "Image of the outer membrane of enteric gram-negaive bacteria by lactoferrin and transferring", Infection and Immunity, vol. 56, No. 11, 1988, pp. 2774-2781.
Groenink et al., "Cationic amphipathic peptides, derived from bovine and human lactoferrins, with antimicrobial activity against oral pathogens", FEMS Microbiology Letters, vol. 179, No. 2, Oct. 15, 1999, pp. 217-222.
Nibbering et al., "Human lactoferrin and peptides derived from its N-terminus are highly effective against infections with antibiotic-resistant bacteria", Infection and Immunity, vol. 69, No. 3, Mar. 2001, pp. 1469-1476.

* cited by examiner

*Primary Examiner*—Bruce R. Campell
*Assistant Examiner*—Roy Teller
(74) *Attorney, Agent, or Firm*—Townsend and Townsend and Crew, LLP

(57) ABSTRACT

The present invention provides polypeptides related to human lactoferrin protein that have utility in a variety of therapeutic and prophylactic applications, including use as antimicrobial agents. The invention further provides pharmaceutical compositions containing these polypeptides and therapeutic methods using such compositions. Methods for detecting antimicrobial infections using the polypeptides are also provided.

41 Claims, 15 Drawing Sheets

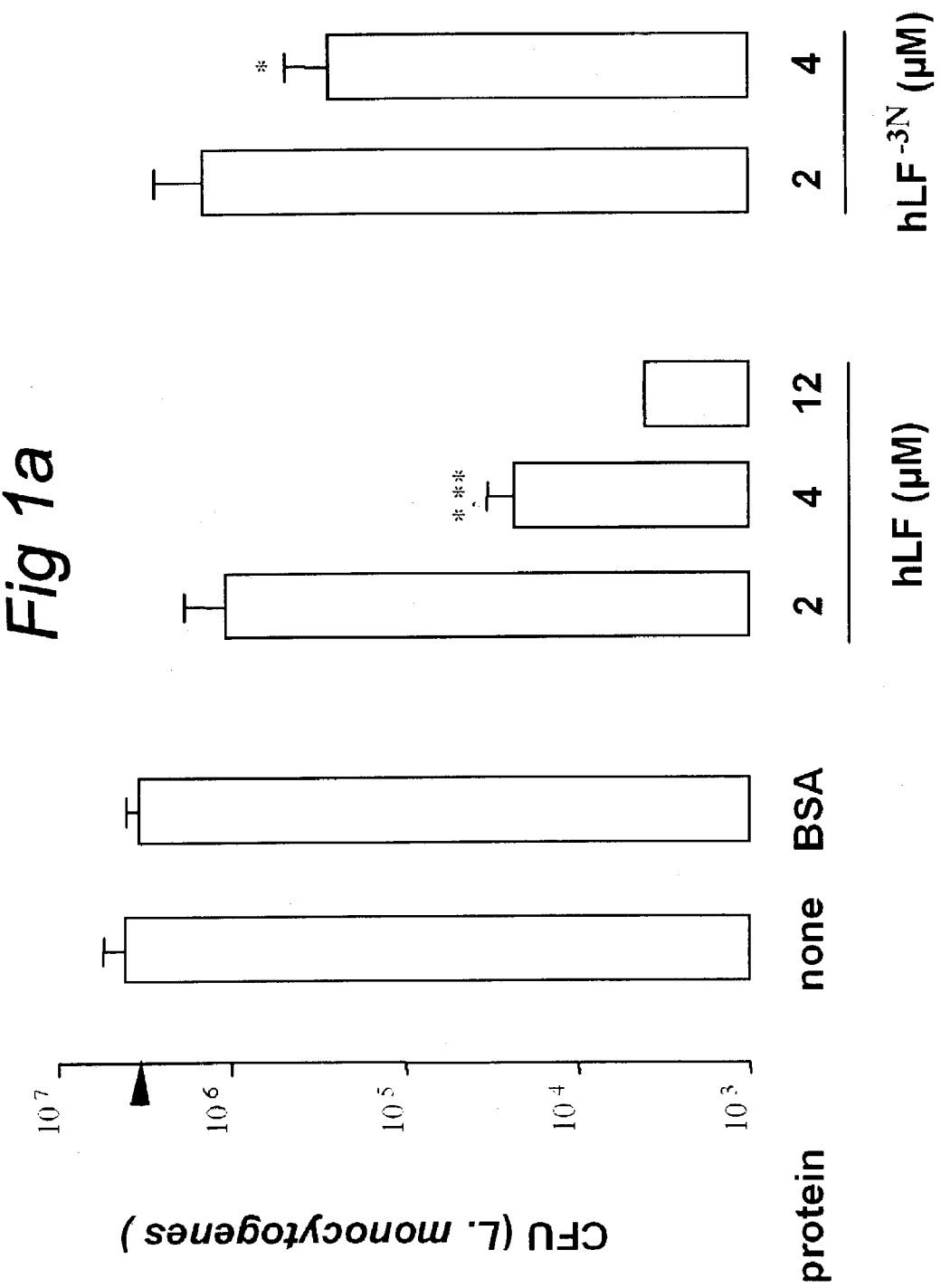

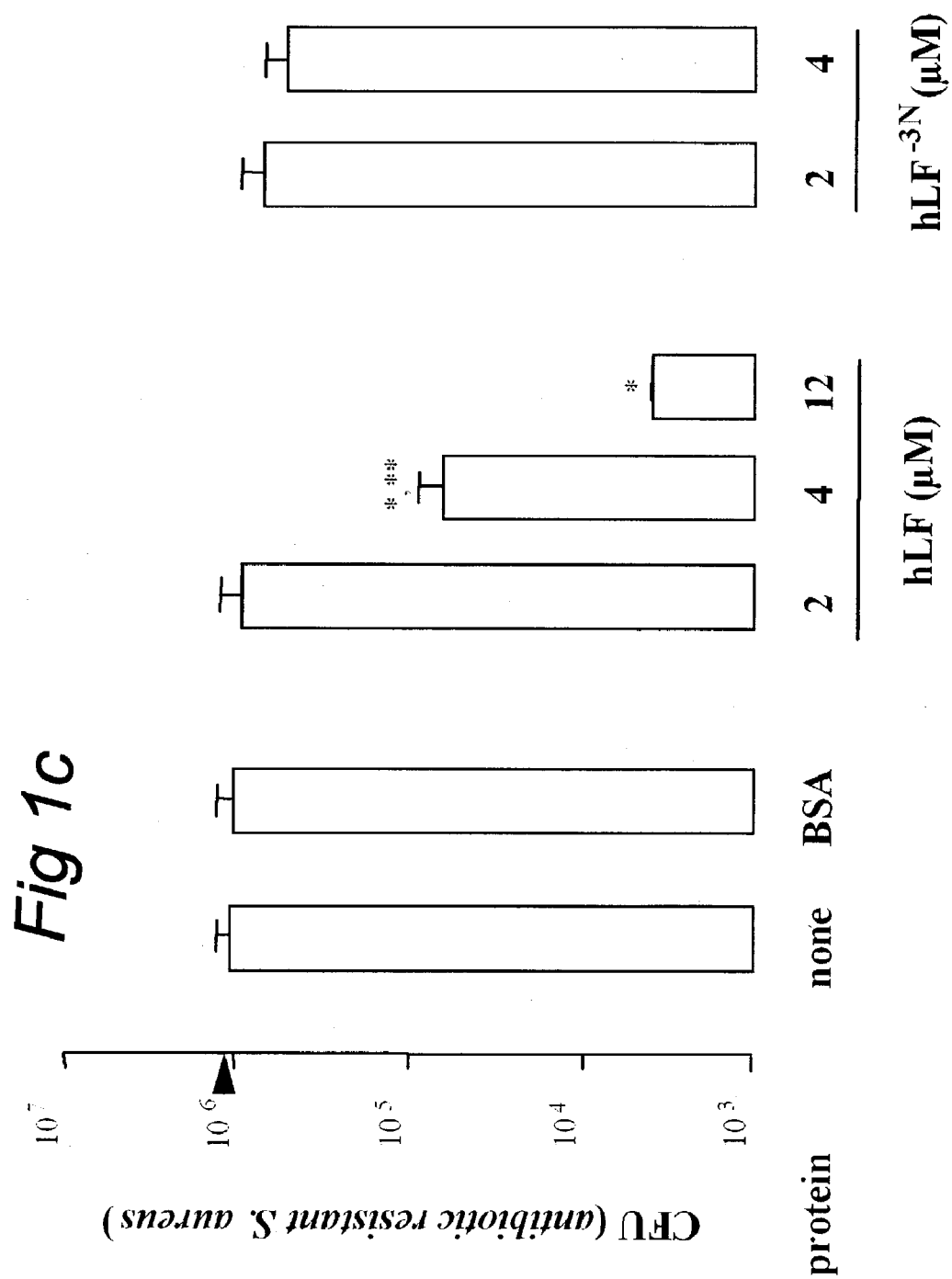

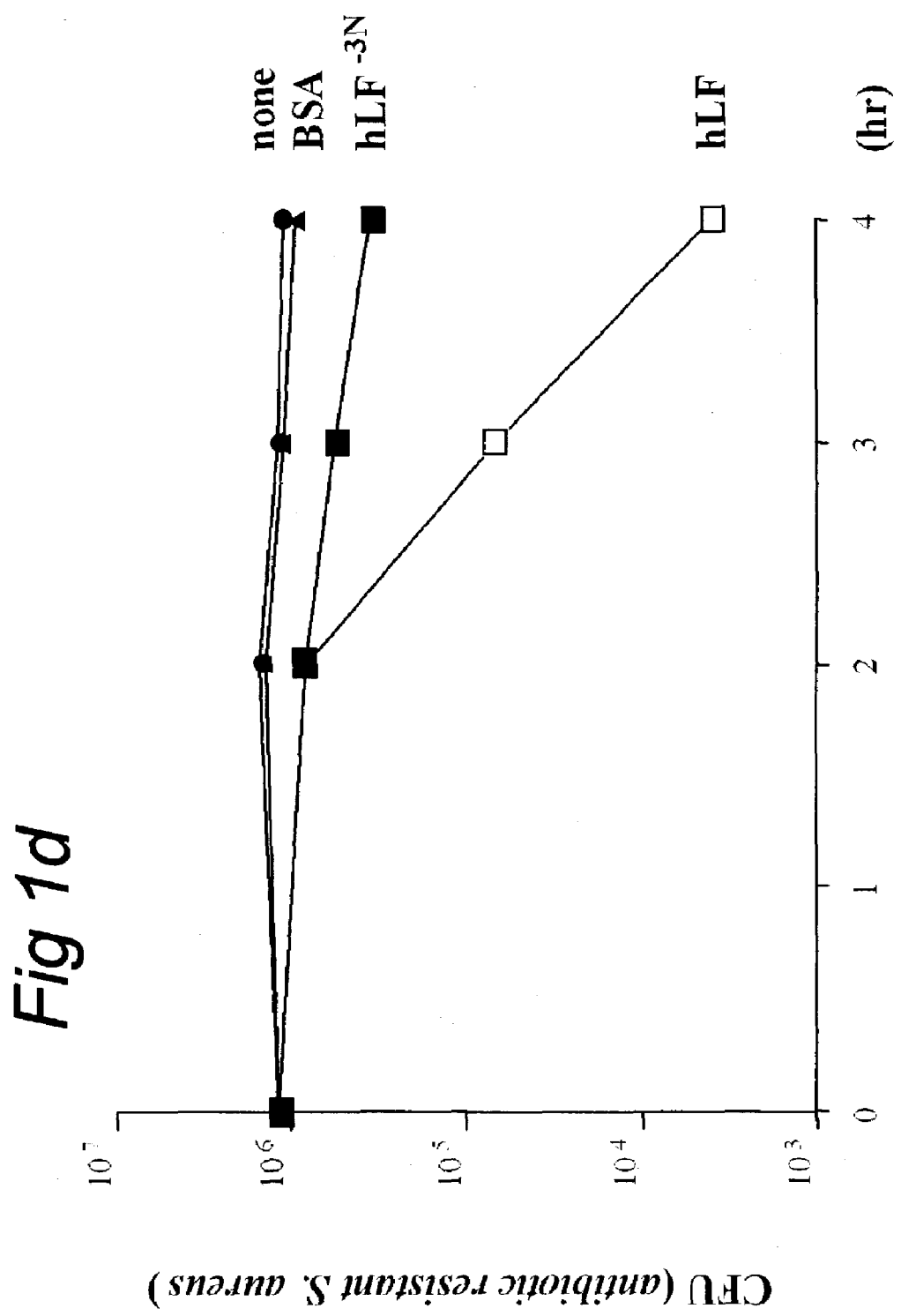

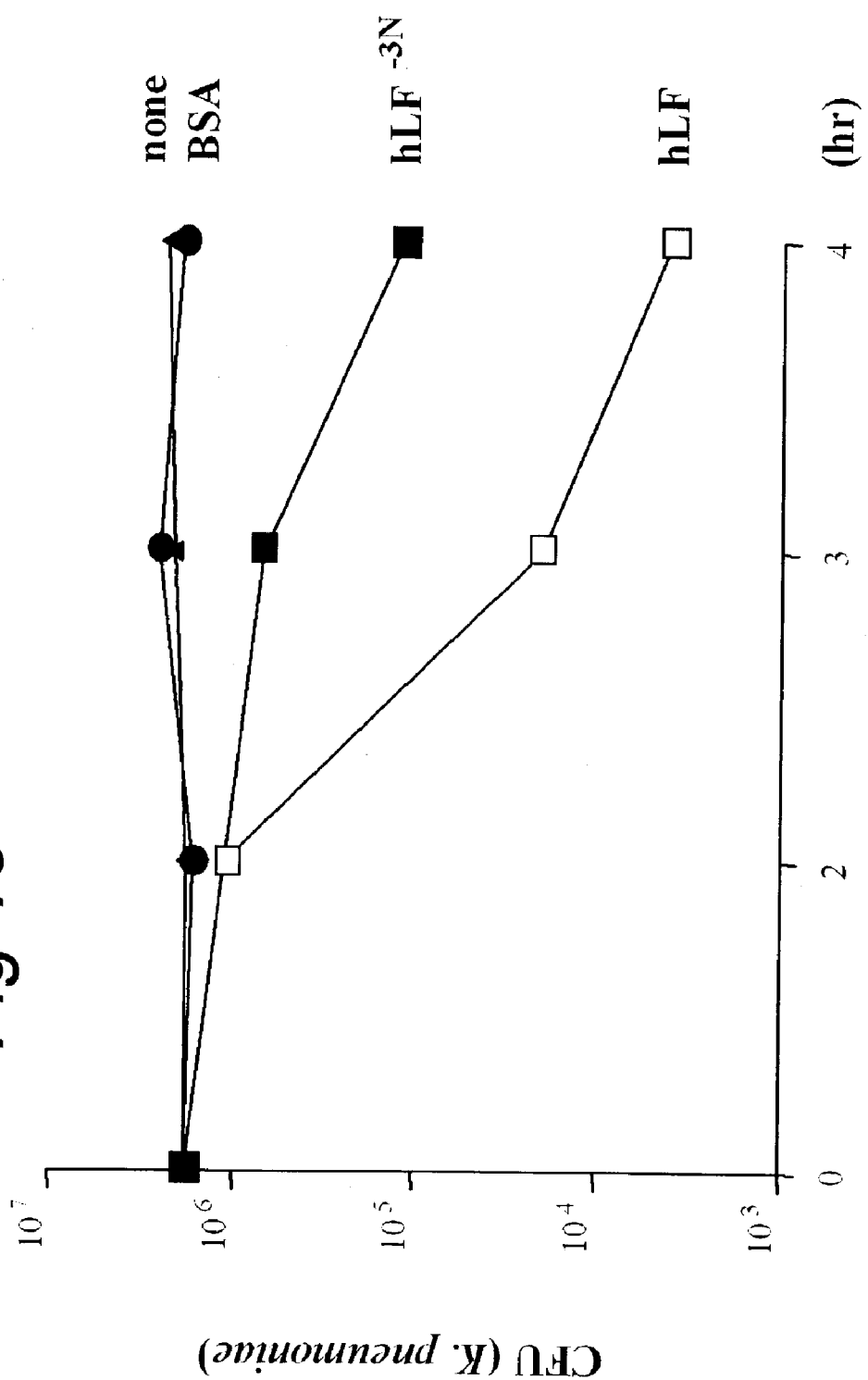

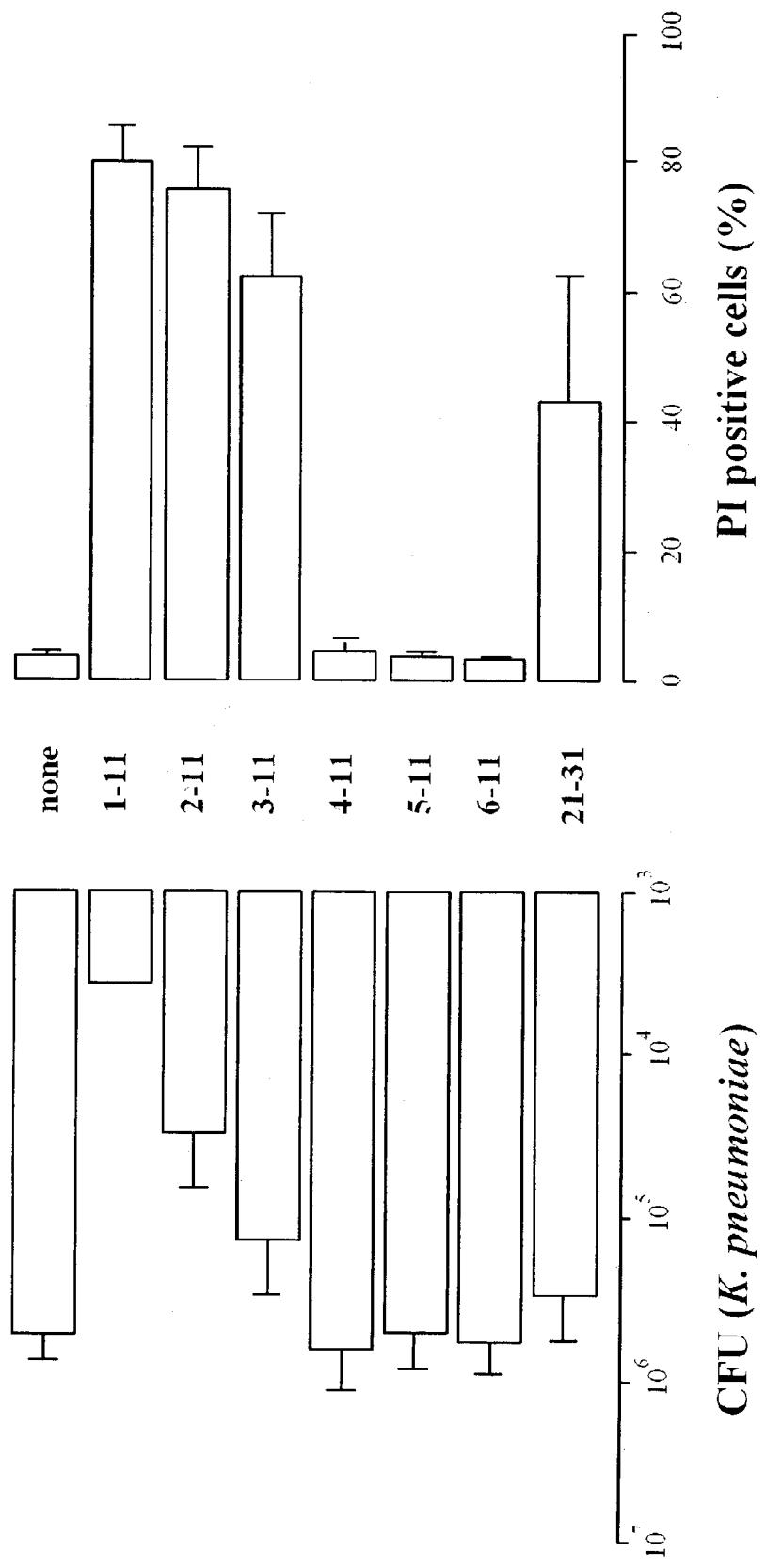

ANTIMICROBIAL ACTIVITY OF THE FIRST CATIONIC CLUSTER OF HUMAN LACTOFERRIN

FIELD OF INVENTION

The present invention relates to the field of polypeptides having various therapeutic and prophylactic applications, including bactericidal activity. As such, the present invention broadly relates to the fields of protein and medicinal chemistry.

BACKGROUND OF THE INVENTION

Lactoferrin (LF) is a metal binding glycoprotein of Mr 77,000 found in milk, tears, saliva, bronchial, intestinal, and other secretions. LF is also present in the secondary granules of neutrophils. Lactoferrin plays an important role in numerous inflammatory and immune response functions such as regulation of monocyte colony stimulating factor synthesis, activation of natural killer cell activity, inhibition of metastasis, and maturation of T-cells. Lactoferrin also inhibits myelopoiesis, binds to members of the low density lipoprotein receptor family, and blocks the clearance of lipoprotein chylomicron remnant particles (2, 32, 33, 34). It also appears to play a role in inhibiting the production or release of prostaglandin $E_2$, interleukins, and tumor necrosis factor by mononuclear cells (35, 36, 37).

Human lactoferrin (hLF) is also a major component of the non-specific defense of mucosal surfaces and neutrophils and is active against a variety of pathogens (reviewed in 1,2). This protein displays antimicrobial properties against Gram-positive and Gram-negative bacteria by limiting the availability of environmental iron (3). However, since iron-saturated hLF is also able to kill certain bacteria (4), mechanisms other than iron-depletion apparently are involved in the antibacterial activity of lactoferrin.

The amino acid sequence of LF has been determined by protein-sequencing and sequencing of cDNA clones. Human LF (hLF) consists of a polypeptide chain of 692 amino acids and contains two N-terminal cationic domains, i.e., RRRR (residues 2–5 of SEQ ID NO:1) and RK VR (residues 28–31 of SEQ ID NO:1), whereas bovine lactoferrin (bLF) has only one cationic domain (residues 17–42 (8,9)). The LF polypeptide is folded into two globular lobes, each of which contains an iron-binding cleft. The high affinity of LF for iron confers to the protein certain antibacterial properties and, in addition, may play a role in the absorption of dietary iron by the small intestine.

It has been reported that peptides of bLF origin (9) as well as synthetic peptides that include the second cationic domain of hLF (12) show antibacterial activity resulting from depolarization of the membrane, increased membrane permeability and metabolic injury. There is considerable controversy over whether hLF binds to bacterial products, such as endotoxin and glycosaminoglycans, through its first (13–15) or second (16,17) cationic domain. One group of researchers has concluded that a loop region consisting of amino acid residues 20 to 37 of hLF is responsible for the antibacterial effect of hLF, whereas residues 1 to 17 at the N-terminal region are not essential (5).

SUMMARY OF THE INVENTION

This invention provides polypeptides and pharmaceutical compositions that are useful in treating a wide variety of microbial infections such as bacterial infections and therapeutic methods for using such compositions.

For example, the present invention provides polypeptides that include at least 6 but no more than 27 contiguous amino acids from the N-terminal segment of human lactoferrin protein (SEQ ID NO:1), wherein the N-terminus of said polypeptide is residue 1 of SEQ ID NO:1. The invention further includes similar polypeptides that include at least 6 but not more than 26 or 25 contiguous amino acids from the N-terminal segment of human lactoferrin protein, wherein the N-terminus of said polypeptide is residue 2 and 3 of SEQ ID NO:1, respectively. Specific examples of polypeptides provided by the invention include hLF(1–11), hLF(2–11) and hLF(3–11).

The present invention further provides a variety of pharmaceutical compositions that in general include a polypeptide as described below and a pharmaceutically acceptable excipient. Certain polypeptides used in some pharmaceutical compositions are no more than 27 amino acids in length, have an N-terminal amino acid sequence of XaaArgArg. (Xaa is any amino acid and Arg is the amino acid arginine) and have antimicrobial activity. Other polypeptides used in other pharmaceutical compositions of the invention are similar to that just described, except they are no more than 26 amino acid residues in length and have an N-terminal sequence of ArgArg. Still other related polypeptides are 25 amino acids or less in length and have an N-terminal Arg. Polypeptides that can be included in other pharmaceutical compositions include any of the polypeptides described herein, including, for example, various N-terminal fragments from hLF (e.g., hLF(1–11), hLF(2–11) and hLF (3–11)).

The invention also provides methods for treating patients suffering from various microbial infections, such as bacterial, viral, fungal or parasitic infections, for example. The methods include administering a therapeutic amount or prophylatically effective amount of a polypeptide or pharmaceutical composition of the invention to a patient.

Methods for detecting microbial infections in a patient are also provided by the invention. These methods typically involve administering a labeled polypeptide to a patient injected with, or suspected of being infected with, a microbe, wherein said polypeptide is human lactoferrin protein (SEQ ID NO:1) or a subsequence thereof capable of interacting with said microbe and detecting the presence of said labeled polypeptide at a site of infection. In one such method, the polypeptide is labeled with a radioisotope and the presence of the radioisotope at the site of infection is visualized with a gamma camera.

The invention further provides methods for altering the permeability of microbial cell membrane by contacting the microbial cell membrane with a polypeptide of the invention.

BRIEF DESCRIPTION OF THE DRAWINGS

FIGS. 1A and 1B are charts depicting the antibacterial activity of natural hLF and hLF$^{-3N}$ (hLF protein without the N-terminal glycine and the two N-terminal arginines, i.e., without residues 1–3 of SEQ ID NO:1) against *L. monocytogenes*, and antibiotic resistant *S. aureus*. FIGS. 1A and 1B illustrate a dose-dependent reduction of the number of viable *L. monocytogenes* (FIG. 1A), and antibiotic resistant *S. aureus* (FIG. 1B) by natural hLF and hLF$^{-3N}$. Tests involved exposing approximately 1–2×10$^6$ CFU of *L. monocytogenes* or antibiotic resistant *S. aureus* to various concentrations of natural hLF or hLF$^{-3N}$ for 3 h at 37° C.; the number of viable bacteria remaining at that point were then determined using standard microbiological techniques. The detection limit was 4,000 CFU. Results are expressed as a mean value (±standard deviation (SD)) and are calculated from at least three separate experiments.

FIGS. 1C–1E show a time-dependent reduction of the number of viable *L. monocytogenes* (FIG. 1C), antibiotic resistant *S. aureus* (FIG. 1D) and *K. pneumoniae* (FIG. 1E) by natural hLF and hLF$^{-3N}$. Approximately 1–2×10$^6$ CFU of the various bacteria were exposed to 4 µM of natural hLF or hLF$^{-3N}$ for various intervals at 37° C., and then the number of viable bacteria determined microbiologically. Results are expressed as a mean value (±SD) and are calculated from at least three separate experiments. The detection limit was 4,000 CFU.

FIGS. 2A–2D are graphs showing the relative abilities of hLF(1–11) (residues 1–11 inclusively from the N-terminus of hLF, i.e., residues 1–11 of SEQ ID NO:1) and fragments thereof, as well as hLF(21–31) (residues 21–31 from the N-terminal region of hLF. i.e., residues 21–31 of SEQ ID NO:1), to kill of *L. monocytogenses* (FIG. 2A), antibiotic resistant *S. aureus* (FIG. 2B), *K. pneumoniae* (FIG. 2C) and *E. coli* (FIG. 2D). Approximately 2×10$^6$ CFU of the various bacteria were exposed to 7 µM of hLF(1–11) or fragments thereof, or to 65 µM of hLF(21–31) for 1 h at 37° C. the number of viable bacteria was then determined microbiologically. Results are expressed as a mean value (±SD) and are calculated from at least three separate experiments. In addition, the effects of the peptides on the membrane permeability of the various bacteria was assessed using 1 µg of propidium iodide/ml and FACS analysis. Results are expressed as a mean value (±SD) and as a percentage of propidium iodide positive bacteria.

DEFINITIONS

Figure 1B:
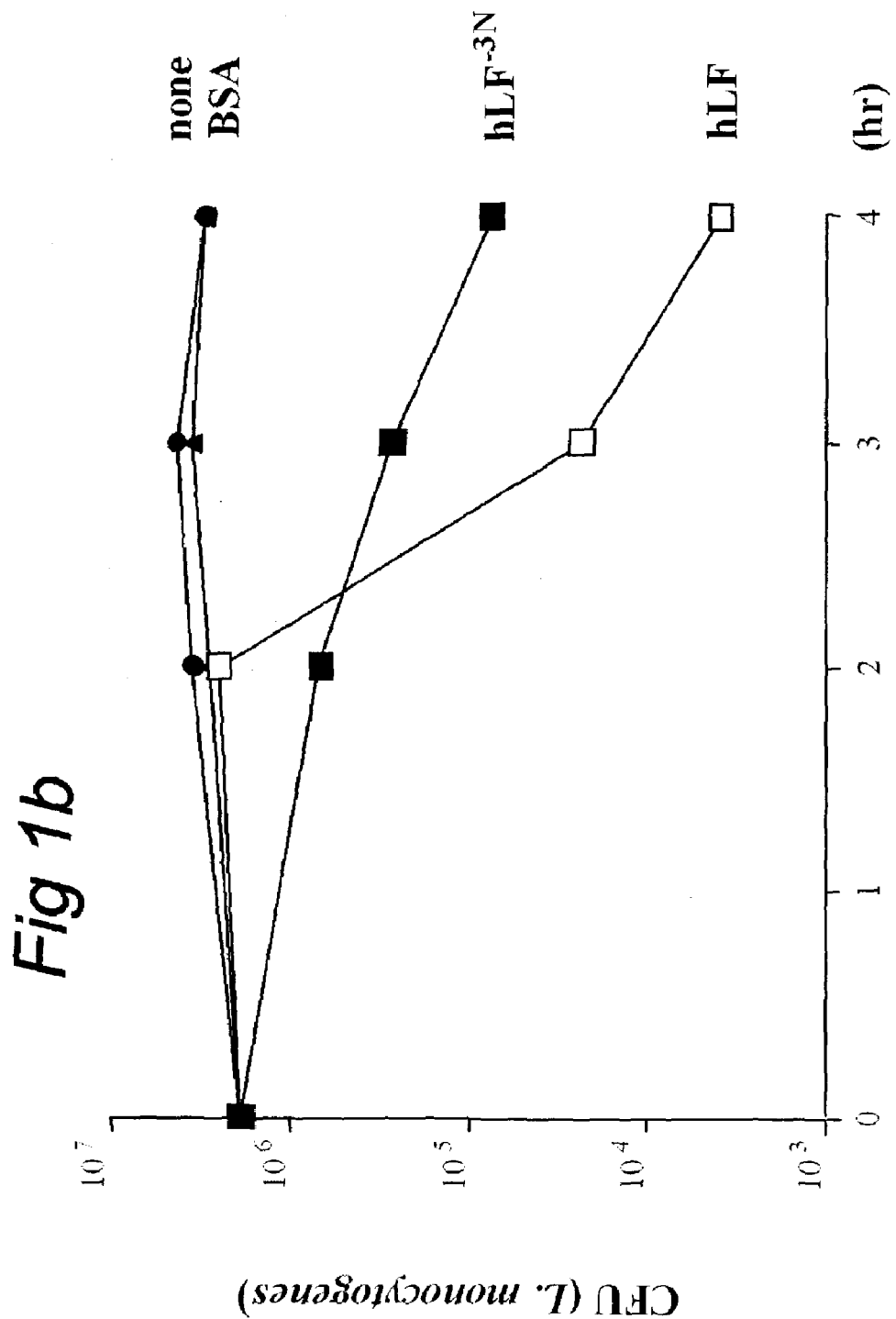
Figure 2A:
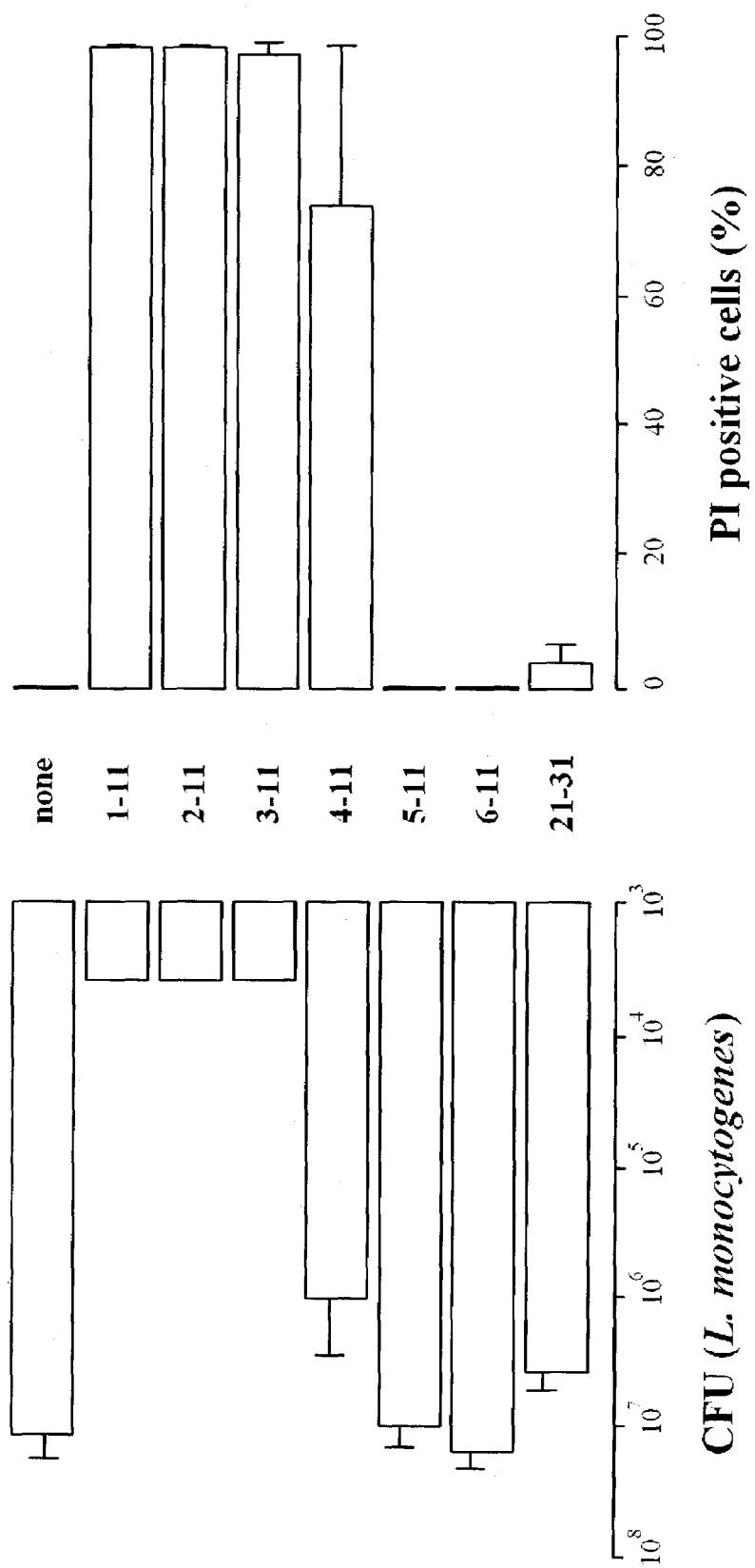
Figure 2B:
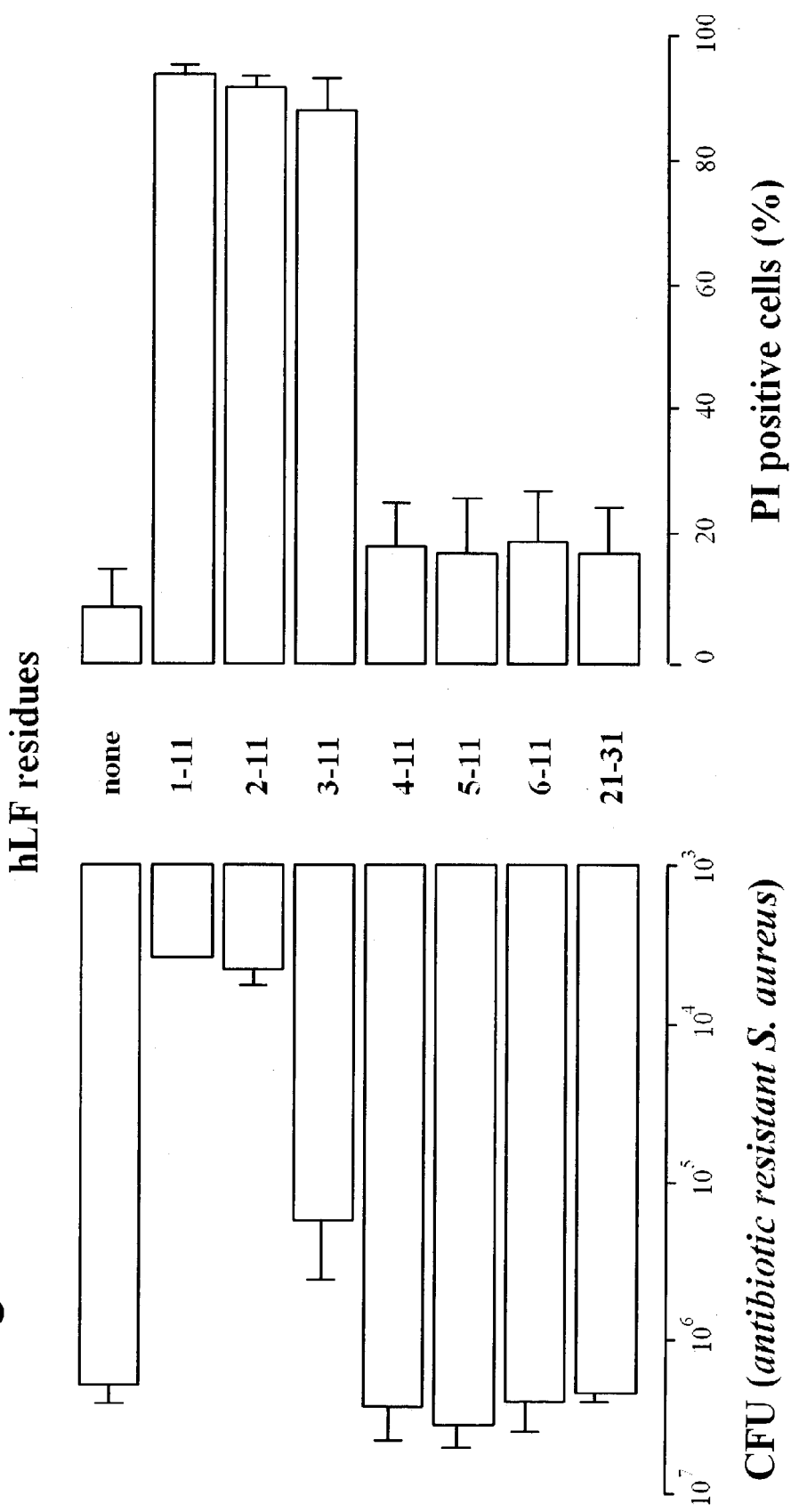
Figure 2D:
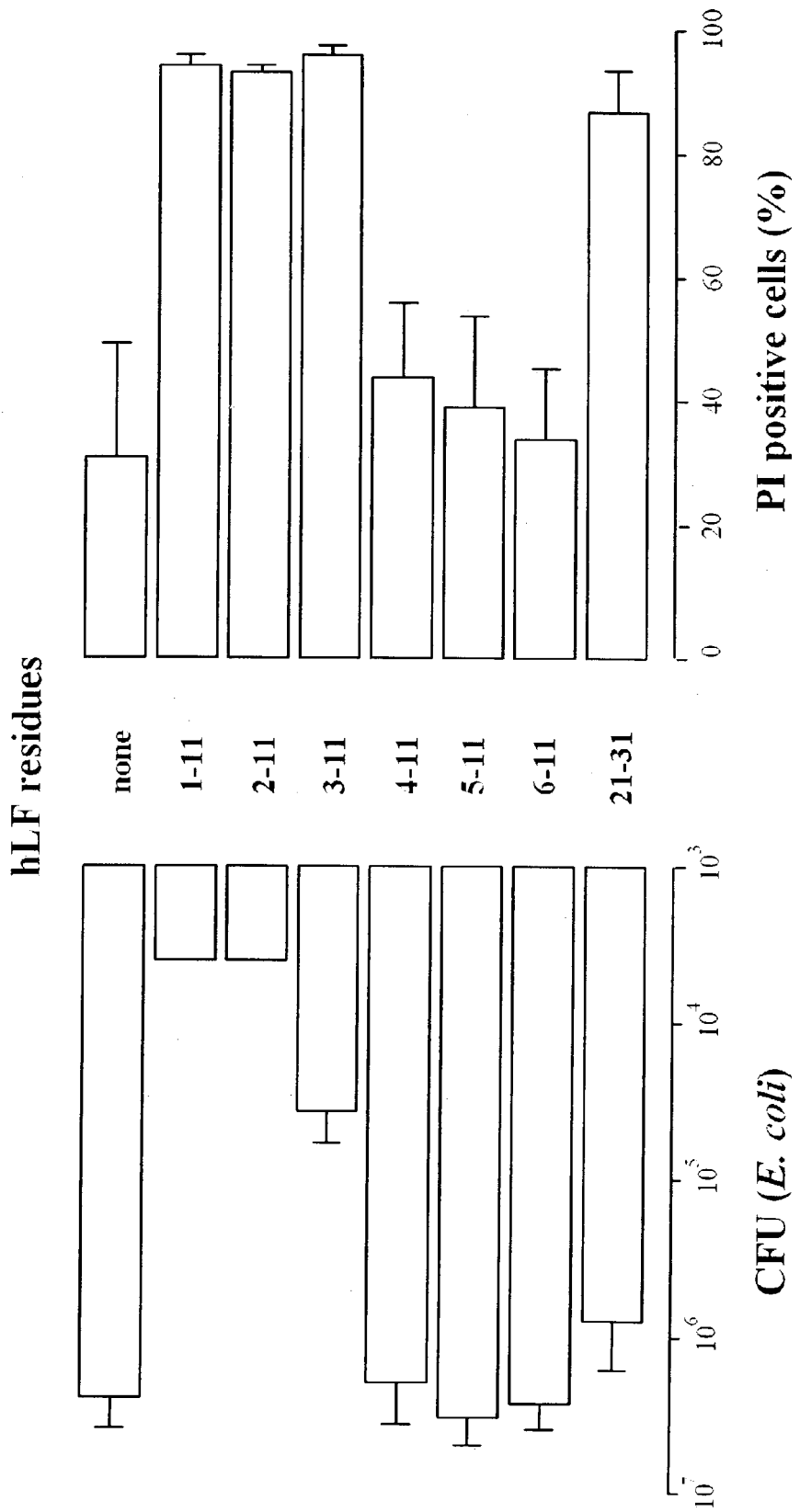

The terms "polypeptide," "peptide" and "protein" are used interchangeably to refer to a polymer of amino acid residues. Unless otherwise stated, the term also applies to amino acid polymers in which one or more amino acids are chemical analogues of a corresponding naturally-occurring amino acid.

The term "human lactoferrin protein," "human lactoferrin," or simply "hLF protein" or "hLF" refers to a full-length human lactoferrin polypeptide, e.g., a polypeptide having an amino acid sequence substantially as described by Powell, M. J. and Ogden, J. E., Nucleic Acids Res. 18:4013 (1990), which is incorporated herein by reference. An exemplary sequence for human lactoferrin protein is the sequence set forth in SEQ ID NO:1. Other related human lactoferrin sequences are provided, for example, by Metz-Boutigue, M. H., et al., Eur. J. Biochem. 145:659–676 (1984), Rado, T. A., et al., Blood 70:989–993 (1987), and Hevneker, H. L., WO 91/08216, each of which is incorporated herein by reference. The term human lactoferrin protein also includes naturally-occurring human allelic variants and variants involving conservative substitutions of amino acids.

The term human lactoferrin protein also includes hLF wherein the protein backbone is modified. Examples of such modifications include acetylations, carboxylation, glycosylation modifications and other processing variants of hLF. For example, natural human lactoferrin includes recombinantly encoded human lactoferrin expressed in a transgenic nonhuman animal, such as a bovine, where the glycosylation pattern may be distinct from glycosylation patterns of naturally-occurring human lactoferrin obtained from human milk.

The term "hLF fragment," "hLF subsequence," or "contiguous amino acid sequence of hLF" refers to a polypeptide wherein the amino acid residues of the polypeptide consist of a contiguous sequence of amino acids from hLF. As with hLF, these terms include polypeptides having conservatively modified variations or chemical modifications (e.g., carboxylation, glycosylation, acetylations) to a subsequence of hLF. The term also includes fragments wherein the cysteine at residue 10 (see SEQ ID NO:1) is conserved, in both fragments Consisting of contiguous sequence of amino acids from hLF as well as fragments having conservative variations.

In a shorthand format for referring to subsequences of hLF, the specific residues being referred to are placed in parentheses. For example, hLF(1–11) refers to residues 1 to 11 inclusively from the N-terminus of hLF; similarly, hLF (2–11) refers to residues 2 to 11 inclusively from the N-terminal region of hLF, hLF (i.e., the full-length protein) that lacks a certain number of residues from the N-terminus is referred to as hLF where x is the number of N-terminal residues missing. Thus, for example, hLF in which the N-terminal glycine and arginine are removed is referred to as hLF$^{-2N}$; hLF missing the N-terminal glycine and the two N-terminal arginines, is referred to as hLF$^{3}$N, and hLF lacking the N-terminal glycine and first three arginine residues is referred to as hLF$^{-4N}$. The three arginines located at the N-terminus (i.e., residues 2, 3 and 4 of SEQ ID NO:1) are referred to as Arg$^2$, Arg$^3$ and Arg$^4$, respectively. Unless otherwise stated, the N-terminal amino acid of hLF refers to Gly$^1$ (see SEQ ID NO:1); the 31 residues located at the amino-terminus of hLF are: N'-GRRRRSVQWCAVSQ-PEATKCFQWQRNMRKVR (residues 1–31 of SEQ ID NO:1).

A "conservative substitution," when describing a protein, refers to a change in the amino acid composition of the protein that does not substantially alter the protein's activity. Thus, "conservatively modified variations" of a particular amino acid sequence refers to amino acid substitutions of those amino acids that are not critical for protein activity or substitution of amino acids with other amino acids having similar properties (e.g., acidic, basic, positively or negatively charged, polar or non-polar) such that the substitutions of even critical amino acids do not substantially alter activity. Conservative substitution tables providing functionally similar amino acids are well-known in the art. See, e.g., Creighton (1984) *Proteins*, W.H. Freeman and Company. In addition, individual substitutions, deletions or additions which alter, add or delete a single amino acid or a small percentage of amino acids in an encoded sequence are also "conservatively modified variations."

The term "naturally-occurring" as applied to an object refers to the fact that an object can be found in nature. For example, polypeptide sequence that is present in an organism that can be isolated from a source in nature and which has not been intentionally modified by humans in the laboratory is naturally-occurring.

The term "isolated," "purified" or "substantially pure" means an object species (e.g., hLF or a fragment thereof) is the predominant macromolecular species present (i.e., on a molar basis it is more abundant than any other individual species in the composition), and preferably the object species comprises at least about 50 percent (on a molar basis) of all macromolecular species present. Generally, the object species in an isolated, purified or substantially pure composition will comprise more than 80 to 90 percent of all macromolecular species present in a composition. Most preferably, the object species is purified to essential homogeneity (i.e., contaminant species cannot be detected in the composition by conventional detection methods) wherein the composition consists essentially of a single macromolecular species.

The phrases "specifically binds to a protein" or "specifically immunoreactive with," when referring to an antibody refers to a binding reaction which is determinative of the presence of the protein in the presence of a heterogeneous population of proteins and other biologics. Thus, under designated immunoassay conditions, a specified antibody binds preferentially to a particular protein and does not bind in a significant amount to other proteins present in the sample. Specific binding to a protein under such conditions requires an antibody that is selected for its specificity for a particular protein. A molecule such as an antibody that specifically binds to a protein has an association constant of at least $10^6$ M$^{-1}$ or $10^7$ M$^{-1}$, preferably $10^8$ M$^{-1}$, to $10^9$ M$^{-1}$, and more preferably, about $10^{10}$ M$^{-1}$ to $10^{11}$ M$^{-1}$ or higher. A variety of immunoassay formats may be used to select antibodies specifically immunoreactive with a particular protein. For example, solid-phase ELISA immunoassays are routinely used to select monoclonal antibodies specifically immunoreactive with a protein. See, e.g., Harlow and Lane (1988) *Antibodies, A Laboratory Manual*, Cold Spring Harbor Publications, New York, for a description of immunoassay formats and conditions that can be used to determine specific immunoreactivity.

The term "patient" includes human and veterinary subjects.

DETAILED DESCRIPTION

I. General

The invention provides polypeptides such as hLF fragments and pharmaceutical compositions utilizing such polypeptides that are useful in a variety of therapeutic and prophylactic applications, including use as antimicrobial agents. The invention is based in part upon the finding that short polypeptides having one or more arginines in the N-terminal segment of the polypeptide, such as found in the first cationic domain of hLF, exhibit significant therapeutic activity.

More specifically, the polypeptides of the invention include one or more residues from the first cationic domain of hLF, but do not include amino acids from the second cationic domain The polypeptides are quite short, generally less than 27 amino acids in length. Given their short lengths the polypeptides are easily and inexpensively prepared and are readily amenable to use in pharmaceutical compositions. Antibodies which specifically bind to the polypeptides of the invention are also provided.

The invention further provides pharmaceutical compositions which include a polypeptide and one or more other components such as a pharmaceutically acceptable excipient. The polypeptide used in the composition is a short polypeptide typically less than 27 amino acids long, has one or more arginine residues in the N-terminal segment, and has antimicrobial activity. Thus, the polypeptide can consist of contiguous sequences from the first cationic domain of hLF, for example.

Methods of treating patients suffering from infections are further provided by the invention. The methods involve administering a therapeutic dose of one of the polypeptides or pharmaceutical compositions of the invention to a patient. The methods are effective against a wide range of microbes, including, for example, viruses and bacteria.

The invention also discloses methods for detecting or imaging microbial infections such as bacterial infections using labeled hLF or fragments thereof which migrate to the site of a microbial infection. Using a detector suitable for the type of label attached to the peptide, it is possible to detect infection sites.

II. Polypeptides

A. General

The invention provides various polypeptides which include at least one or more arginines from the first cationic domain of hLF (residues 2–5 of SEQ ID NO:1), but which exclude the residues which make up the second cationic domain (residues 28–31 of SEQ ID NO:1). Thus, for example, the invention provides polypeptides which comprise at least 6 but no more than 27 contiguous amino acids from the N-terminal segment of hLF (SEQ ID NO:1), wherein the N-terminus of the polypeptide is residue 1 of SEQ ID NO:1, i.e., glycine.

The invention further includes similar polypeptides that include the first cationic domain but not the second cationic domain of hLF, and that also lack one or more residues from the N-terminus of hLF. For example, the invention also includes polypeptides comprising at least 6 amino acids but no more than 26 contiguous amino acids from hLF, wherein the N-terminus of the polypeptide is Arg² (for example, a hLF fragment lacking Gly¹). The invention also includes polypeptides comprising at least 6 but no more than 25 contiguous amino acids from the N-terminal segment of hLF, wherein the N-terminus of the polypeptide is Arg³ (for example, a hLF fragment lacking Gly¹ Arg²).

In some instances, the hLF polypeptide fragments just described are chosen so that cysteine residue 10 (see SEQ ID NO:1) is retained. In other cases, the polypeptide includes a cysteine at approximately the same location in the sequence. Such a cysteine can be used to dimerize one fragment with another polypeptide having, a cysteine residue, such as another hLF fragment, for example. In some instances, dimerization can increase the activity of the polypeptide.

The minimum length of the polypeptides may include more than 6 contiguous amino acids from the N-terminus of hLF. For example, some polypeptides of the invention may include 7, 8, 9, 10, 11 or 12 contiguous amino acids from hLF, for example. The polypeptides may also include fewer than 27, 26 or 25 contiguous amino acids of hLF. For instance, the polypeptides of the invention may include less than 24, 29, 20, 18, 16, 14 or 12 contiguous amino acids from hLF, or any number of amino acids therebetween. In some instances, the polypeptide includes no more than 19 contiguous amino acids from hLF. In other instances, the polypeptide includes no more than 11 contiguous amino acids from hLF. For example, as described further in the Examples, polypeptides of the invention include hLF(1–11), hLF(2–11) and hLF(3–11).

B. Preparation of Polypeptides

Particularly because the polypeptides of the invention are relatively short, the polypeptides can be readily synthesized using known methods. For example, the polypeptides can be synthesized by the well-known Merrifield solid-phase synthesis method in which amino acids are sequentially added to a growing chain. See Merrifield (1963). *J. Am. Chem. Soc.* 85:2149–2156; and Atherton et al., "Solid Phase Peptide Synthesis," IRL Press. London, (1989). Automatic peptide synthesizers are commercially available from numerous suppliers, such as Applied Biosystems, Foster City, Calif. Additional synthetic approaches for preparing the polypeptides of the invention are described in Example I below.

Certain polypeptides of the invention can also be prepared via a reduction and proteolysis method. This approach begins with pepsin digestion of hLF according to known methods (see. e.g., Bellamy, W. et al. *Biochim. Biophys. Acta.* 1121:130–136 (1992); and Tomita, M. et al., *J. Dairy Sci.* 74:4137–4132 (1991)). In order to break the disulfide bond between Cys 10 and Cys 46, the digested products are subsequently reduced and alkylated using standard reagents (e.g., DTT or β-mercaptoethanol for reduction and iodoacetamine or 4-vinylpyridine for alkylation) according to known methods (see, e.g., "Current Protocols in Protein Chemistry." (Coligan, J. E. et al. Eds.) John Wiley and Sons, Inc. The order can be reversed so that the reduction and alkylation steps precede the pepsin digestion step. After digestion, reduction and alkylation, N-terminal peptides can be isolated from the digestion mixture by standard chromatographic methods, including for example, cation exchange, gel filtration, HIC or RP-HPLC.

Alternatively, the polypeptides of the invention can be prepared using well-known recombinant techniques in which a nucleotide sequence encoding the polypeptide of interest is expressed in cultured cells such as described in Ausubel et al., *Current Protocols in Molecular Biology*, Greene Publishing and Wiley-Interscience, New York (1987) and in Sambrook et al., *Molecular Cloning—Laboratory Manual*, 2nd ed. vols. 1–3, Cold Spring Harbor Laboratory, Cold Spring Harbor, N.Y. 1989, both of which are incorporated herein by reference in their entirety. Also see, Kunkel. 1985, *Proc. Natl. Acad. Sci.* 82:488 (describing site directed mutagenesis) and Roberts et al., 1987, *Nature* 328:731–734 or Wells, J. A., et al. (1985) *Gene* 34:315 (describing cassette mutagenesis).

Typically, nucleic acids encoding the desired polypeptides are used in expression vectors. The phrase "expression vector" generally refers to nucleotide sequences that are capable of affecting expression of a gene in hosts compatible with such sequences. These expression vectors typically include at least suitable promoter sequences and optionally, transcription termination signals. Additional factors necessary or helpful in effecting expression may also be used as described herein. DNA encoding the polypeptides of the present invention will typically be incorporated into DNA constructs capable of introduction into and expression in an in vitro cell culture. Specifically, DNA constructs will be suitable for replication in a prokaryotic host, such as bacteria, e.g., *E. coli*, or may be introduced into a cultured mammalian, plant, insect, yeast, fungi or other eukaryotic cell lines.

DNA constructs prepared for introduction into a particular host will typically include a replication system recognized by the host, the intended DNA segment encoding the desired polypeptide, and transcriptional and translational initiation and termination regulatory sequences operably linked to the polypeptide encoding segment. A DNA segment is "operably linked" when it is placed into a functional relationship with another DNA segment. For example, a promoter or enhancer is operably linked to a coding sequence if it stimulates the transcription of the sequence. DNA for a signal sequence is operably linked to DNA encoding a polypeptide if it is expressed as a preprotein that participates in the secretion of the polypeptide. Generally. DNA sequences that are operably linked are contiguous, and, in the case of a signal sequence, both contiguous and in reading phase. However, enhancers need not be contiguous with the coding sequences whose transcription they control. Linking is accomplished by ligation at convenient restriction sites or at adapters or linkers inserted in lieu thereof.

The selection of an appropriate promoter sequence generally depends upon the host cell selected for the expression of the DNA segment. Examples of suitable promoter sequences include prokaryotic, and eukaryotic promoters well-known in the art. See, e.g. Sambrook et al., *Molecular Cloning: A Laboratory Manual* (2d ed.), vols. 1–3, Cold Spring Harbor Laboratory (1989). The transcriptional regulatory sequences will typically include a heterologous enhancer or promoter which is recognized by the host. The selection of an appropriate promoter will depend upon the host, but promoters such as the trp, lac and phage promoters, tRNA promoters and glycolytic enzyme promoters are known and available. See Sambrook et al. supra.

Conveniently available expression vectors which include the replication system and transcriptional and translational regulatory sequences together with the insertion site for the polypeptide encoding segment may be employed. Examples of workable combinations of cell lines and expression vectors are described in Sambrook et al., supra, and in Metzger et al., *Nature* 334:31–36 (1988). For example, suitable expression vectors may be expressed in, e.g., insect cells, e.g., Sf9 cells, mammalian cells. e.g. CHO cells and bacterial cells, e.g., *E. coli*.

In certain instances, the polypeptides of the invention are produced by expression in transgenic animals (i.e., nonhuman animals containing an exogenous DNA sequence in the genome of germ-line and somatic cells introduced by way of human intervention) such as bovines, goats, rabbits, sheep, pigs or mice. Methods for production of recombinant polypeptides by transgenic nonhuman species are known in the art and are described, for example, in U.S. Pat. Nos. 5,304,489; 5,633,076; and 5,565,362 which are incorporated herein by reference in their entirety, as well as in PCT publications PCT/US93/05724 and PCT/US95/09580, both of which are incorporated herein by reference in their entirety. An advantage of the transgenic animals is the isolation of the polypeptides of interest in large amounts, especially by economical purification methods. For example, the production of transgenic bovine species containing a transgene encoding a human lactoferrin polypeptide targeted for expression in mammary secreting cells is described in WO 91/08216, incorporated herein by reference in its entirety. When lactoferrin variants are produced in transgenic bovines the human protein typically is separated from the bovine milk proteins (e.g., whey proteins, caseins, bovine lactoferrin, IgA, albumin, lysozyme, β-lactoglobulin) before use (e.g., administration to patients). Alternatively, use may be made of whole or partially purified bovine milk containing the desired polypeptide.

Another method for preparing the polypeptides of the invention is to employ an in vitro transcription/translation system. DNA encoding a polypeptide of the invention is cloned into an expression vector as described supra. The expression vector is then transcribed and translated in vitro. The translation product can be used directly or first purified. Polypeptides resulting from in vitro translation typically do not contain the post-translation modifications present on polypeptides synthesized in vivo. Methods for synthesis of polypeptides by in vitro translation are described by, for example, Berger & Kimmel. *Methods in Enzymology, Volume 152, Guide to Molecular Cloning Techniques*, Academic Press, Inc., San Diego, Calif., 1987 (incorporated herein by reference in its entirety).

III. Pharmaceutical Compositions

A. Utility

The polypeptides and pharmaceutical compositions of the invention exhibit a number of biological activities that provide benefit in therapeutic or prophylactic applications. For example, as described in greater detail in the Examples below, the compositions are useful in treating various microbial infections such as bacterial infections. The polypeptides and pharmaceutical compositions may also have various other beneficial activities. These include anti-inflammatory, anti-viral and anti-infective activities, as well a pro- and anti-coagulant effects, modulation of complement activation, inhibition of lipoylpolysaccharide-(LPS) mediated activation of neutrophils, and growth promotion of intestinal epithelial cells. Other properties and biological activities of lactoferrin are described in Nuijens et al., 1996, *J. Mammary Gland Biology and Neoplasia* 1:3, 283–293, which is incorporated herein by reference in its entirety.

Therapeutic indications for the pharmaceutical compositions described herein include use in therapy or prophylaxis of infection, including local infection, large scale (bacterial) infection, blood-borne infection (sepsis), as well as inflammation resulting from an infection or non-infectious inflammatory diseases (e.g., chronic inflammatory disease of the ileum or colon). The compositions can also be used to prepare or treat organ transplant recipients or other immunosuppressed individuals (e.g., AIDS patients) against the effects of infections.

The pharmaceutical compositions are effective in treating a variety of microbial infections, such as various viral, bacterial and fungal infections. For example, the compositions are effective in treating Gram-negative and Gram-positive bacteria. More specifically, some examples of pathogenic bacteria causing infections treatable by methods of the invention include: *Listeria, Escherichia, chlamydia, rickettsial* bacteria, *mycobacteria, staphylococci, treptocci, pneumonococci, meningococci* and *conococci, Klebsiella, proteus, serratia, pseudomonas, Legionella, diphtheria, salmonella, bacilli, cholera, tetanus, botulism, anthrax, plague, leptospirosis,* and *Lymes* disease bacteria.

Some examples of pathogenic viruses causing infections treatable by methods of the invention include: hepatitis (A. B, or C), herpes virus (e.g. VZV, HSV-I, HAV-6, HSV-II, and CMV, Epstein Barr virus), adenovirus, influenza virus, flaviviruses, echovirus, rhinovirus, coxsackie virus, coronavirus, respirator, syncytial virus (RSV), mumps virus, rotavirus, measles virus, rubella virus, parvovirus, vaccinia virus, HTLV virus, dengue virus, papillomavirus, molluscum virus, polio virus, rabies virus, JC virus, arboviral encephalitis virus, and human immunodeficiency virus (HIV virus; e.g., type I and II).

Some examples of pathogenic fungi causing infections treatable by methods of the invention include: *Candida* (e.g., *albicans, krusei, glabrata, tropicalis*), *Cryptococcus neoformans, Aspergillus* (e.g., *fumigatus, niger*). Genus *Mucorales* (*Mucor, Absidia, Rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include: *Entamoeba histolytica, Balantidium coli, Naegleria, Fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondii* and *Plasmodium falciparis*.

The efficacy of the polypeptides and pharmaceutical compositions of the invention may be further improved by combining the use of the compositions of the invention with compositions for treating microbial infections known in the art per se. As such, the polypeptides and compositions of the invention may be combined with e.g. penicillins such as amplicillin, cephalosporins, erythromycin, kanamycin, gentamicin, vancomycin or tetracyclines, for treating bacterial infections. For treating viral infections they may be combined with antiviral nucleoside analogs such as aclycovir, ganciclovir, zidovudine (AZT) or didanosine. Similarly, for treating fungal infection the polypeptides and compositions of the invention may be combined with amphotericin B, nystatin, miconazole, fluconazole, clotrimazole, terbinafine, naftifine or butenafine.

B. Composition

The particular form of the composition varies with the intended mode of administration and therapeutic application. Typically, however, the composition includes a polypeptide and a pharmaceutically acceptable excipient, wherein the polypeptide has a defined length, consists of one or more arginine residues at the N-terminus and has antimicrobial activity (e.g. is effective in killing viruses or bacteria). In certain compositions, the polypeptide includes a contiguous segment of up to 27 amino acids and the N-terminal amino acids of the polypeptide consists of the residues XRR (where X is any amino acid and R is arginine). The invention also includes compositions in which the polypeptide is no longer than 26 amino acids and the N-terminal amino acids are RR. Also included by the invention are compositions in which the polypeptide is no longer than 25 amino acids and the N-terminus is R (i.e. Arg). In other instances, the polypeptide is shorter, such as 5, 10, 15, 20 or 25 amino acids long, or any length therebetween. The polypeptide is even smaller in other compositions. For instance, the polypeptide may simply consist of the N-terminal XRR or RR residues. The polypeptides used in the pharmaceutical compositions can also include any of the polypeptides described above.

While the N-terminus of the polypeptide consists of the amino acids XRR, RR or R, the remaining contiguous amino acid sequence of the polypeptide sequence can vary so long as the polypeptide has antimicrobial, activity. For example, the remaining contiguous sequence can consist of a contiguous amino acid sequence from hLF, especially the sequence beginning after $Arg^3$. Thus, as described in the Examples below, the polypeptide can be hLF(1–1), hLF(2–11) or hLF(3–11). When the polypeptide used in the pharmaceutical composition consists of a contiguous amino acid sequence from the N-terminal segment of hLF, the amino acid sequence may include sequences wherein a small number (e.g., one, two or three) amino acids are inserted or removed from the hLF sequence. Alternatively, the polypeptide includes contiguous sequences from hLF, wherein one or more of the amino acids has been chemically modified.

The compositions may also include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS. Ringer's solution, dextrose solution, and Hank's solution. In addition, the pharmaceutical composition or formulation may also include other carriers, adjuvants, or non-toxic, nontherapeutic, nonimmunogenic stabilizers, excipients and the like. The compositions may also include additional substances to approximate physiological conditions, such as pH adjusting and buffering agents, toxicity adjusting agents, wetting agents, detergents and the like. Because of the ability of hLF to bind iron, in some instances it may be beneficial to include iron in the pharmaceutical composition.

The composition may also include any of a variety of stabilizing agents, such as an antioxidant for example. Moreover, the polypeptides may be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include the production of sulfate, gluconate, citrate, phosphate and the like. The polypeptides of the composition may also be complexed with molecules that enhance their in vivo attributes. A list of such molecules, provided by way of example and not limitations includes carbohydrates, polyamines, amino acids, other peptides, ions (e.g., sodium, potassium, calcium, magnesium, manganese), and lipids.

Further guidance regarding formulations that are suitable for various types of administration can be found in *Remington's Pharmaceutical Sciences*, Mace Publishing Company, Philadelphia, Pa., 17th ed. (1985). For a brief review of methods for drug delivery, see, Langer, *Science* 249: 1527–1533 (1990). Both of these references are incorporated herein by reference in their entirety.

The compositions containing the polypeptides can be administered for prophylactic and/or therapeutic treatments.

The polypeptide in the pharmaceutical composition typically is present in a therapeutic amount, which is an amount sufficient to remedy a disease state or symptoms, particularly symptoms associated with a microbial infection, or otherwise prevent, hinder, retard, or reverse the progression of disease or infection or any other undesirable symptoms in any way whatsoever. The concentration of the polypeptide in the pharmaceutical composition can vary widely, i.e., from less than about 0.1% by weight, usually being at least about 1% by weight, to as much as 20% by weight or more.

In therapeutic applications, compositions are administered to a patient already suffering from a disease, as just described, in an amount sufficient to cure or at least partially arrest the symptoms of the disease or infection and its complications. An appropriate dosage of the pharmaceutical composition or polypeptide of the invention is readily determined according to any one of several well-established protocols. For example, animal studies (e.g., mice, rats) are commonly used to determine the maximal tolerable dose of the bioactive agent per kilogram of weight. In general, at least one of the animal species tested is mammalian. The results from the animal studies can be extrapolated to determine doses for use in other species, such as humans for example.

What constitutes an effective dose also depends on the nature and severity of the disease or condition, and on the general state of the patient's health, but will generally range from about 1 to 500 mg of purified protein per kilogram of body weight, with dosages of from about 5 to 100 mg per kilogram being more commonly employed.

In prophylactic applications, compositions containing the compounds of the invention are administered to a patient susceptible to or otherwise at risk of a particular disease or infection. Such an amount is defined to be a "prophylactically effective" amount or dose. In this use, the precise amounts again depends on the patient's state of health and weight. Typically, the dose ranges from about 1 to 500 mg of purified protein per kilogram of body weight, with dosages of from about 5 to 100 mg per kilogram being more commonly utilized.

The pharmaceutical compositions described herein can be administered in a variety of different ways. Illustrative examples include administering a composition containing a pharmaceutically acceptable carrier via oral, intranasal, rectal, topical, intraperitoneal, intravenous, intramuscular, subcutaneous, subdermal, transdermal, intrathecal, and intracranial methods. The preferred formulation and delivery option typically varies depending upon the location and size of the area requiring treatment. For example, for localized infections, the formulation may be designed for topical application or localized injection, for example. Systemic reactions, in contrast, may be treated or prevented by administration of compositions formulated for parenteral administration.

For oral administration, the active ingredient can be administered in solid dosage forms, such as capsules, tablets, and powders, or in liquid dosage forms, such as elixirs, syrups, and suspensions The active component(s) can be encapsulated in Gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

If desired, for example in the treatment of infections or disorders of the digestive tract or even for general oral administration of the compositions, it is possible to formulate solid or liquid formulations in an enteric-coated or otherwise protected form. In the case of liquid formulations, the formulation can be mixed or simply coadministered with a protectant, such as a liquid mixture of medium chain triglycerides, or the formulation can be filled into enteric capsules (e.g., of soft or hard gelatin, which are themselves optionally additionally enteric coated). Alternatively, solid formulations comprising the polypeptide can be coated with enteric materials to form tablets. The thickness of enteric coating on tablets or capsules can be, for example, from 0.5 to 4 microns in thickness. The enteric coating may comprise any of the enteric materials conventionally utilized in orally administrable pharmaceutical formulations. Suitable enteric coating materials are known, for example, from *Remington's Pharmaceutical Sciences*, Mace Publishing Company. Philadelphia, 17th ed. (1985); and *Hagars Handbuch der Pharmazeutischen Praxie*, Springer Verlag, 4th ed., Vol. 7a (1971), both of which are incorporated herein by reference in their entirety.

Another delivery option involves loading the composition into lipid-associated structures (e.g., liposomes, or other lipidic complexes) which may enhance the pharmaceutical characteristics of the polypeptide component of the composition. The complex containing the composition may subsequently be targeted to specific target cells by the incorporation of appropriate targeting molecules (e.g., (specific antibodies or receptors). It is also possible to directly complex the polypeptide with a targeting agent.

Compositions prepared for intravenous administration typically contain 100 to 500 ml of sterile 0.9% NaCl or 5% glucose optionally supplemented with a 20% albumin solution and 100 to 500 mg of a polypeptide of the invention. A typical pharmaceutical composition for intramuscular injection would be made up to contain, for example, 1 ml of sterile buffered water and 1 to 10 mg of the purified polypeptide of the invention. Methods for preparing parenterally administrable compositions are well-known in the art and described in more detail in various sources, including, for example, *Remington's Pharmaceutical Science*, Mack Publishing, Philadelphia, Pa., 17th ed., (1985) (previously incorporated herein by reference in its entirety).

Particularly when the compositions are to be used in vivo, the components used to formulate the pharmaceutical compositions of the present invention are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Any of the above pharmaceutical compositions may in addition to the polypeptides of the invention comprise one or more further antimicrobial agents known in the art per se. For treating bacterial infections the pharmaceutical compositions may, in addition to the polypeptides of the invention, comprise antibiotics such as amplicillin, cephalosporins, erythromycin, kanamycin, gentamicin, vancomycin and/or tetracyclines. For treating viral infections the pharmaceutical compositions may, in addition to the polypeptides of the invention, comprise antiviral nucleoside analogs such as aclycovir, ganciclovir, zidovudine (AZT) and/or didanosine. Similarly, for treating fungal infections the pharmaceutical compositions may, in addition to the polypeptides of the invention, comprise amphotericin B, nystatin, miconazole, fluconazole, clotrimazole, terbinafine, naftifine and/or butenafine.

III. Methods of Detecting Microbial Infections

Methods for detecting microbial infections such as bacterial infections are also provided by the invention The method typically involves administering a labeled polypeptide to a patient infected with, or suspected of being infected with some type of microbial organism. The polypeptide is hLF or a fragment thereof which is capable of interacting with the organism. Because the labeled polypeptide is capable of interacting with the infectious organism it accumulates at the site of infection. It is possible to detect the accumulation of the polypeptide al a site of infection using various detectors which are sensitive to the label that is attached to the polypeptide.

The polypeptide used can vary, but includes the polypeptides of the invention described herein. In addition to these N-terminal fragments, however, hLF, as well as other fragments (i.e., fragments other than the N-terminal fragments described above) which are capable of binding to microbial organisms such as bacteria can also be utilized. As described further in Example VI, hLF(1–11), hLF(2–11) and hLF (3–11) rapidly accumulate at the site of infection.

The label utilized to label the polypeptide can vary widely; the label simply needs to be a molecule or macromolecule that is capable of generating a detectable signal and that can be attached to the polypeptide. Illustrative examples of such molecules include radioactive isotopes, fluorophors, chromophores, electron dense reagents, magnetic particles, enzymes, and ligands having a specific binding partner (e.g., biotin).

Similarly, the detector used to detect the label can be any device which is capable of detecting the signal generated by the label. For example, when the polypeptide is labeled with a radioactive isotope, the detector can include a gamma camera. Using such a camera it is possible to obtain images of the site of infection which can be utilized in various research, diagnostic and therapeutic applications.

IV. Screening Methods

The invention further provides methods for screening polypeptides to determine which of the polypeptides containing one or more amino acids from the first cationic domain of hLF but lacking residues from the second cationic domain have antimicrobial activity. Screening can be performed using in vitro or in vivo methods. In vitro methods generally involve mixing a suspension containing the bacteria of interest with a solution containing the test polypeptide. Typically, several different concentrations of the test polypeptide are tested. At various different time intervals, the number of viable bacteria are determined using standard microbiological techniques. Results are compared with control solutions which contain no polypeptide at all or contain a polypeptide known not to have antibacterial activity. Additional details regarding this approach are set forth in Example II below.

The in vivo methods generally involve injecting a test animal (e.g., a mouse or rat) with a known amount of bacteria suspended in a test solution. Control animals are infected with a solution containing no polypeptide or a solution containing a polypeptide which is known to have no antimicrobial activity. The bacteria are allowed to grow for a set period of time and then the test animals are sacrificed. Infected tissue is removed and the number of bacteria present in the infected tissue is determined using standard microbiological techniques. Example II below provides more specifics regarding one in vivo method.

V. Other Uses/Activities

The polypeptides of the present invention have various activities associated with the first cationic cluster of hLF. For example, the polypeptides of the invention are especially useful in selectively triggering responses involving the first cationic domain while avoiding the activation of responses associated with the binding of the second cationic domain and/or activities related to the iron binding activities of hLF.

Some polypeptides of the invention can bind and neutralize heparin and lipopolysaccharide (LPS), lipid A, and DNA and human lysozyme. Certain polypeptides provided herein can also bind to various target cells. Lactoferrin binds to cell surfaces through two classes of LF binding sites: relatively low affinity sites which are cell surface sulfated molecules (e.g., cell surface proteoglycans or glycosaminoglycans) and high affinity receptors Since binding of LF to the low affinity sites involves the first cationic domain, some polypeptides of the present invention can selectively bind to the low affinity sites without activating the LF high affinity receptors. Thus, for example, some polypeptides of the present invention are useful in neutralizing heparin or lipopolysaccharide (LPS) without activating the lactoferrin high affinity receptor. In the case of heparin, certain polypeptides can neutralize the anticoagulant activity of heparin (including low molecular weight heparin) By neutralizing bacterial lipopolysaccharides, certain polypeptides of the invention can reduce the inflammatory response associated with these compounds. Cell binding assays are well-known and are described in, e.g., Mazurier, 1989, *Eur. J. Biochem.* 179: 481–87.

Cells which the polypeptides can interact with include, intestinal cells (Hu et al., 1990, *Biochemistry* 29:535–541; Kawakam et at, 1991, *Am. J. Physiol.* 261:G841–G846; Mikogami et at, 1994, *Am. J. Physiol.* 267:G308–G31), mammary gland epithelial cells (Rochard et al, 1992, *Anticancer Res.* 1:2047–2052), hepatocytes (Regoeczi et al. 1985, *Am. J. Physiol.* 248:G8–G14; MacAbee et al. 1991, *J. Biol. Chem.* 226:23624–23631; Ziere et al, 1992, *J. Biol. Chem.* 267:11229–11235), monocytes (Ismail et al, 1993. *J. Biol. Chem.* 268:21618–21625), activated lymphocytes (Mazurier et al, 1989, *Eur. J. Biochem.* 179, 481–487) and platelets (Leveugle et at, 1993. *Eur. J. Biochem.*, 213: 1205–1121), each of which is incorporated by reference in their entirety for all purposes.

Various polypeptides and compositions of the invention can also be used to inhibit entry into a cell of viruses, for example, CMV (cytomegalovirus), HIV (human immunodeficiency viruses) or HSV 1 (herpes simplex virus 1) viruses. Thus, methods of the invention include administering a polypeptide of the invention to a patient to protect against infection by viruses. While not intending to be limited to this particular explanation, the antiviral action is thought to be mediated by interaction of hLF with cell surface proteoglycans (e.g., heparin) employed by viral particles for cell entry, and/or by the stimulation of natural killer cells.

Certain polypeptides are also useful in reducing inflammation. This can occur, as noted above, through neutralization of bacterial lipopolysaccharides, as well as through a reduction in cytokine production and neutrophil degranulation.

In other aspects, the invention provides methods in which some polypeptides and pharmaceutical compositions of the invention are administered to a patient to inhibit myelopoieses and reduce production of GM-CSF.

VI. Antibodies

The invention further provides antibodies which specifically bind to the polypeptides of the invention. Monoclonal antibodies are made from the polypeptides of the invention or from antigen-containing fragments thereof by methods that are well-known in the art (see, e.g., Kohler, et al. Nature, 256:495, (1975); and Harlow & Lane, *Antibodies, A Laboratory Manual* (C.S.H.P., NY, 1988), both of which are incorporated herein by reference in their entirety). The antibodies of the invention are useful in purifying polypeptides of the invention, in screening cDNA expression libraries, and for identifying clones containing cDNA inserts which encode structurally-related, immunocrossreactive polypeptides.

The following examples are presented to further illustrate certain aspects of the invention and are not to be construed so as to limit the scope of the invention.

EXAMPLE I

Materials

A. Lactoferrin and Synthetic Peptides

Natural hLF (Mr 77,000) was purified from the fresh milk of a single donor by cationic exchange chromatography using S-Sepharose (14). The N-terminus of the protein was intact, as determined by N-terminal analytical Mono-S chromatography and N-terminal Edman degradation and sequencing. Human lactoferrin free of contamination with endotoxin and human lysozyme (14) and pure by SDS PAGE, was dialyzed against saline and stored at −70° C. at concentrations of approximately 20 mg/ml. A hLF variant lacking the first three N-terminal residues (GRR), further referred to as hLF$^{-3N}$, was isolated from natural hLF treated with trypsin as described (18). Bovine serum albumin (BSA, Sigma Chem Co. St. Louis, Mo.) was applied instead of hLF or hLF$^{-3N}$ as a control. Synthetic peptides corresponding to residues 1–11 of hLF (GRRRRSVQWCA (residues 1–11 of SEQ ID NO:1–SEQ ID NO: 2); Mr 1,374), further referred to as hLF(1–11), and fragments thereof, and a peptide corresponding to residues 21–31 of hLF (FQWQRNM-RKVR (residues 21–31 of SEQ ID NO:1–SEQ ID NO: 4); Mr 1,548), referred to as hLF(21–31), were prepared and purified as described (19). Purity of the synthetic peptides usually exceeded 88%, as determined by reverse-phase high performance liquid chromatography (RP-HPLC). Stocks of synthetic peptides at a concentration of 1 mM in 5% (v/v) HAc (pH 6.0) were stored at −20° C. and immediately before use were dried in a SPEED-VAC (Savant Instruments Inc, Farmingdale, N.Y.). As controls, protegrin-1 (RGGRLCY-CRRRFCVCVVGR (SEQ ID NO: 5) positive control) and peptide 4 (PPVVSTQLLNGSLAEEEVV (SEQ ID NO: 6) part of gp120 protein from HIV-1 as negative control) were synthesized.

B. Bacteria

Antibiotic resistant *Staphylococcus aureus* strain 2141, a clinical isolate (Dept. of Infectious Diseases, LUMC), was resistant to a panel of antibiotics including methicillin and displayed only limited sensitivity to teicoplanin and rifampicin. *Listeria monocytogenes* strain EGD. *Klebsiella pneumoniae* (43816), and *Escherichia coli* O54 were purchased from the American Type Culture Collection (Rockville, Md.). Antibiotic resistant *S. aureus, K. pneumoniae* and *E. coli* were cultured overnight in nutrient broth (Oxoid, Basingstoke, UK) at 37° C., diluted in tryptase soya broth (TSB, Oxoid) and cultured for an additional 2 h in a shaking waterbath at 37° C. *L. monocytogenes* was cultured overnight in brain heart infusion broth (BHI, Oxoid) at 37° C. diluted and cultured for an additional 2 h in a shaking waterbath at 37° C.

EXAMPLE II

Experimental Methods

A. Assay for Antibacterial Activity of Lactoferrins and Related Polypeptides

An in vitro assay was used to assess the antibacterial activity of hLF and related peptides. In short, bacteria were washed with phosphate-buffered saline (PBS) (pH 7.4) and diluted to a concentration of approximately $2 \times 10^6$ CFU/ml of phosphate-buffered saline (pH 6.0) supplemented with 0.1% (v/v) Tween-20 (hereafter designated as PBS-Tw). Equal volumes of this bacterial suspension and PBS-Tw containing various concentrations of hLF or related synthetic peptides were mixed. At various time intervals (range 0–4 h) after incubation at 37° C. the number of viable bacteria was determined microbiologically. As negative controls, bovine serum albumin (BSA; Sigma) or no peptide were included. Preliminary experiments revealed that the antibacterial activity of synthetic peptides in 10 mM sodium phosphate (pH 7.4; NaPB) supplemented with 1% v/v TSB, further referred to as NaPB-TSB, was ten times more potent in killing bacteria as compared to experiments performed in PBS-Tw (results not shown). Therefore all in vitro antibacterial activities of synthetic peptides were assessed in NaPB-TSB. All other details were as described for natural hLF and hLF$^{-3N}$.

B. Assay for Membrane Permeability

Changes in the membrane permeability of bacteria upon exposure to hLF, hLF$^{-3N}$ and related peptides were monitored after incubation with propidium iodide (PI; Sigma), using FACS analysis (12, 20). Stock solutions of PI (1 mg/ml of deionized water) were prepared. Approximately $2 \times 10^6$ bacteria/ml of PBS-Tw were incubated for various intervals at 37° C., washed, incubated for 5 min with 1 µg of PI/ml (final concentration) and then analyzed with a FACScan (Becton & Dickinson, CA) equipped with a argon-laser at 488 nm. The photomultiplier voltages were routinely set at 500 V for PI fluorescence intensity in the second channel. Data acquisition and analysis were controlled using the Lysis II software.

C. Assay for Non-Specific Esterase Activity

As an indication of intracellular effects of hLF, hLF$^{-3N}$ and related peptides (e.g., hLF (1–11) and hLF(21–31)) in bacteria, the non-specific esterase activity of bacteria upon exposure to these antimicrobial proteins/peptides was assessed using 5-sulfofluorescein diacetate (SFDA; Molecular Probes, Leiden, The Netherlands) and FACS analysis (21). For these experiments, a stock solution of SFDA (1 mg/ml of ethanol) was prepared. Approximately $2 \times 10^6$ CFU of bacteria/ml of PBS-Tw were incubated with various concentrations of hLF, hLF$^{-3N}$ and hLF related peptides for various intervals at 37° C., washed, incubated with 100 µM of SFDA/ml (final concentration ethanol 20% v/v) for 20 min at room temperature in the dark and then analyzed with a FACScan using the photomultiplier voltage of the first channel set at 700 V.

D. Labeling of Lactoferrin and Related Peptides with $^{99m}$Tc

Lactoferrins and related peptides were labeled with $^{99m}$Technetium ($^{99m}$Tc) as described (22, 23). Briefly, 10 µl of a peptide solution (1 mg/ml of HAc) was added to 2 µl of an aseptic solution of 0.5 mg of stannous pyrophosphate/ml (Dept. of Clinical Pharmacy and Toxicology. Leiden University Medical Center (LUMC). Leiden. The Netherlands). Immediately thereafter, 4 µl of a solution of 10 mg of KBH$_4$ (crystalline. Sigma) per ml of 0.1 M NaOH was added. After addition of 0.1 ml of $^{99m}$Tc-sodium pertechnetate solution (200 MBq/ml. Mallinckrodt Medical BV, Petten, The Netherlands), the mixture was gently stirred at ambient temperature for 30 min and then was ready for use. Quality control of the labeling was performed by RP-HPLC analysis using a Sep-Pak C18 cartridge (Waters, Milford, Mass.) in 20 ml of 0.01 M HAc. After rinsing with 20 ml of 0.01 M HAc, proteins and peptides were eluted with 2 ml of methanol (Sigma). Labeling yields amounted to 88–95%.

E. Experimental Thigh Infections

All animal studies were done in compliance with the LUMC Ethical Committee and Dutch laws related to the conduct of animal experiments. Our interest was to assess whether hLF, hLF$^{-3N}$, and related peptides displayed antimicrobial activity in vivo, a well-established animal model for experimental thigh infections was used (23). In short, specific pathogen-free, male. Swiss mice weighing 20–25 g (Broekman Institute, Someren, The Netherlands) were anaesthetized with a single intraperitoneal injection of 0.1 ml of saline containing 1 mg fluanisone and 0.03 mg fentanyl citrate (Hypnorm, Janssen Pharmaceutics, Tilburg, The Netherlands). Preceding scintigraphy, a subcutaneous injection of 0.1 ml, containing 0.2 mg diazepam (Valium, Hoffmann-La Roche, Mijdrecht, The Netherlands) was administered. Immediately thereafter, $1 \times 10^7$ CFU of antibiotic resistant *S. aureus* or *K. pneumoniae* in 0.1 ml of saline were injected into the right thigh muscle, Twenty-four hours thereafter, 0.2 ml of saline, containing various amounts of $^{99m}$Tc-hLF or radiolabeled peptides (0.3–30 µmol), were injected intravenously. As a control, mice were injected with 0.2 ml of saline containing BSA or saline without any peptide. At 24 h after injection of hLF or related peptides, the mice were sacrificed by an intraperitoneal injection of 0.25 ml of saline containing 12 mg of sodium pentobarbital (Sanofi BV. Div. Algin. Maassluis, The Netherlands). Next, the infected thigh muscles were removed and, after weighing, homogenized in 4 ml of PBS. Appropriate dilutions of the homogenates were applied onto diagnostic sensitivity test plates (Oxoid), and the number of colonies counted after an overnight culture at 37° C. Results are expressed as the number of CFUs per gram of infected tissue. All negative cultures were assigned the values of 100 CFU/ml of homogenate, which is the lower limit of detection.

F. Pharmacology

Pharmacology of the radiolabeled hLF preparations and related peptides in antibiotic resistant *S. aureus* infected mice was assessed performing scintigraphy utilized the $^{99m}$Tc-labeled peptides described above. The mice were placed in supine position on a planar gamma camera (Toshiba GCA 7100/UI. Tokyo, Japan) with both hind legs spread out and fixed with surgical tape. Continuous whole body acquisitions of the mice of each 60 s during the first hour after injection of the tracer were made with the gamma camera, equipped with a low-energy general purpose parallel-hole collimator. The camera was connected to a computer (GMS 5500 UI, Toshiba) and high-resolution images of the animals were stored as a 256×256 matrix. The energy peak was set at 140 keV with a window of 20%.

On the scintigrams, anatomically adjusted regions of interest (ROI) were drawn over the various organs and both thighs providing data about clearance of $^{99m}$Tc-peptides and accumulation at the site of infection. The clearance of $^{99m}$Tc-labeled hLF or related peptides from the circulation during the first hour after injection was assessed by determining the half-life ($t_{1/2}$) of radioactivity in ROI drawn over the heart at various time intervals. The amount of radioactivity in the heart was corrected for decay and expressed as a percentage of injected dose (% ID). Accumulation of hLF and related peptides at the site of infection is expressed as the ratio of the counts in the infected (target) and the non-infected thigh muscle (non-target), further referred to as the T/NT ratio.

G. Statistical Analysis

Differences between the values for hLF, hLF$^{-3N}$ and BSA as well as for the various hLF-related peptides and the negative control peptide were analyzed using the Mann-Whitney U-test. The level of significance was set at $p<0.05$.

EXAMPLE III

Antimicrobial Activity of hLF, hLF$^{-3N}$ and Related Synthetic Peptides

This experiment was designed to compare the antibacterial activity of hLF$^{-3N}$ and natural hLF and to identify which N-terminal amino acids from hLF were important in killing bacteria. Antimicrobial activity was determined as described in Example II. As shown in FIGS. 1A–1E, the results revealed that both forms of hLF killed *L. monocytogenes* and antibiotic resistant *S. aureus* and *K. pneumoniae* in a dose-dependent fashion, hLF being more potent ($p<0.05$) than hLF$^{-3N}$ (FIGS. 1A–1B). In addition, natural hLF was faster ($p<0.05$) than hLF$^{-3N}$ in killing these bacteria (FIGS. 1C–1E). In contrast, *E. coli* was not killed by hLF or hLF$^{-3N}$ (Table 1), even at concentrations up to 12 µM (results not shown).

Figure 3A:
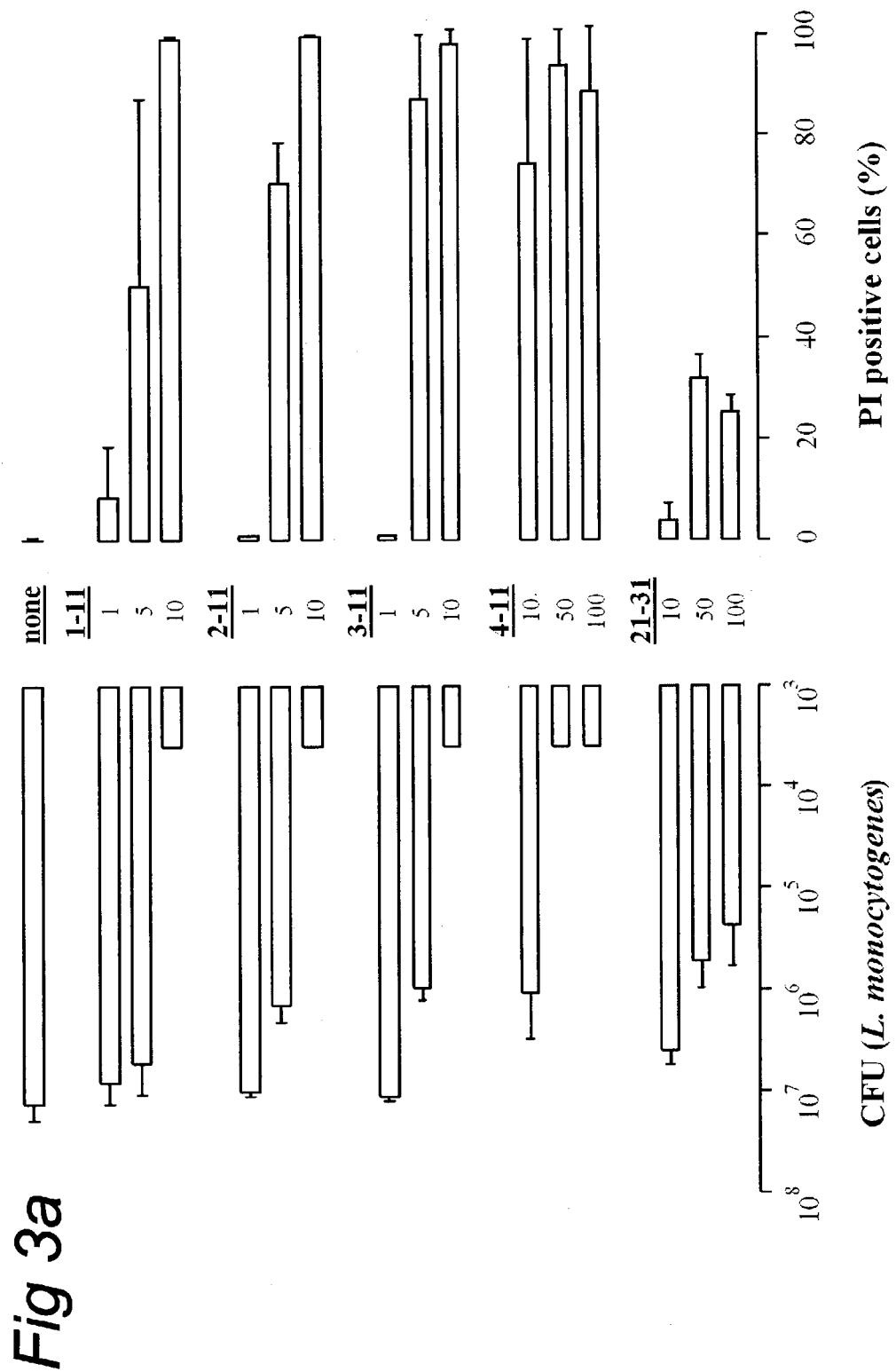
FIGS. 3A–3C illustrate the effect of hLF(1–11) and fragments thereof and hLF(21–31) on *L. monocytogenes* (FIG. 3A), antibiotic resistant *S. aureus* (FIG. 3B), and *E. coli* (FIG. 3C). Approximately 1×10$^6$ CFU of the various bacteria were exposed to increasing micromolar concentrations of these peptides for 1 h at 37° C. The number of viable bacteria was determined microbiologically and the percentage of propidium iodide-positive bacteria was determined by FACS analysis. Results are expressed as a mean value (±SD) and are calculated from at least three separate experiments.
Figure 3B:
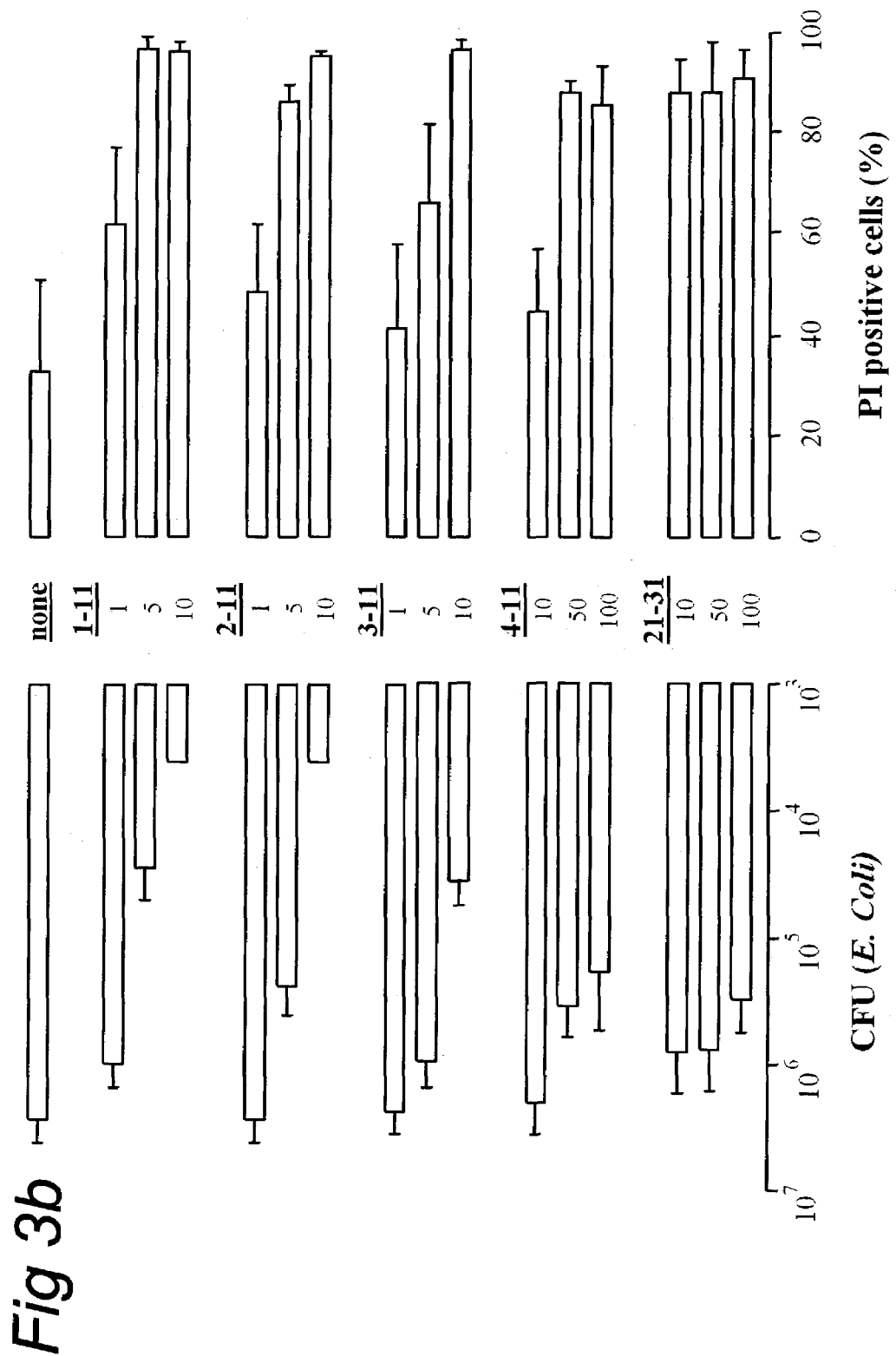
Figure 3C:
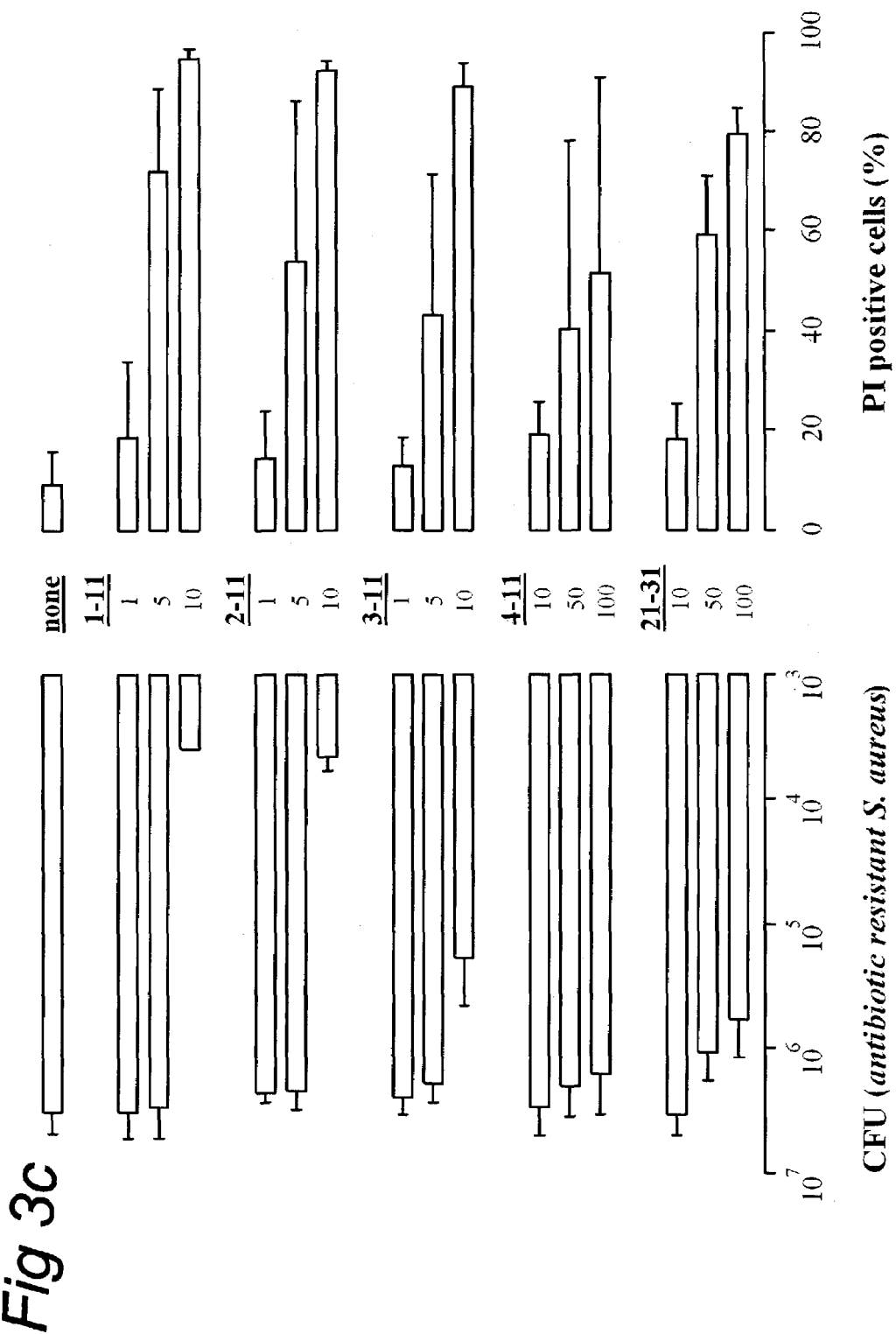

To find out which N-terminal amino acids of hLF are important for killing of bacteria, the in vitro antibacterial effects of synthetic peptides corresponding to the first eleven N-terminal residues of hLF and fragments thereof were determined, again according to the methods set forth in Example II. The results revealed that hLF(1–11), hLF(2–11), hLF(3–11), and hLF(4–11) displayed bactericidal activity against the various bacteria, whereas hLF(5–11) and hLF(6–11) were ineffective (See FIGS. 2A–2D). Dose-effect studies revealed that hLF(1–11) and hLF(2–11) were considerably ($p<0.05$) more efficient than hLF(3–11), which was significantly ($p<0.05$) more efficient than hLF(4–11) in killing *L. monocytogenes* and antibiotic resistant *S. aureus* (See FIGS. 3A–3C). These data indicate that the first two arginines are important for the bactericidal activity of hLF against these bacteria, and that at least one of these arginines is critical for the bactericidal activity of the polypeptides. In addition, hLF(1–11), hLF(2–11) and hLF(3–11), but not the other peptides killed *K pneumoniae* and *E. Coli* (FIGS. 2A–2D and 3A–3C). The bactericidal activities of hLF (21–31), which includes the second cationic domain of hLF, and hLF(1–11) was then determined against *L. monocytogenes*, antibiotic resistant *S. aureus* and *E. coli*. The results revealed that hLF(1–11) is at least ten times more ($p<0.05$) efficient than hLF(21–31) (FIGS. 3A–3C).

EXAMPLE IV

Figure 4:
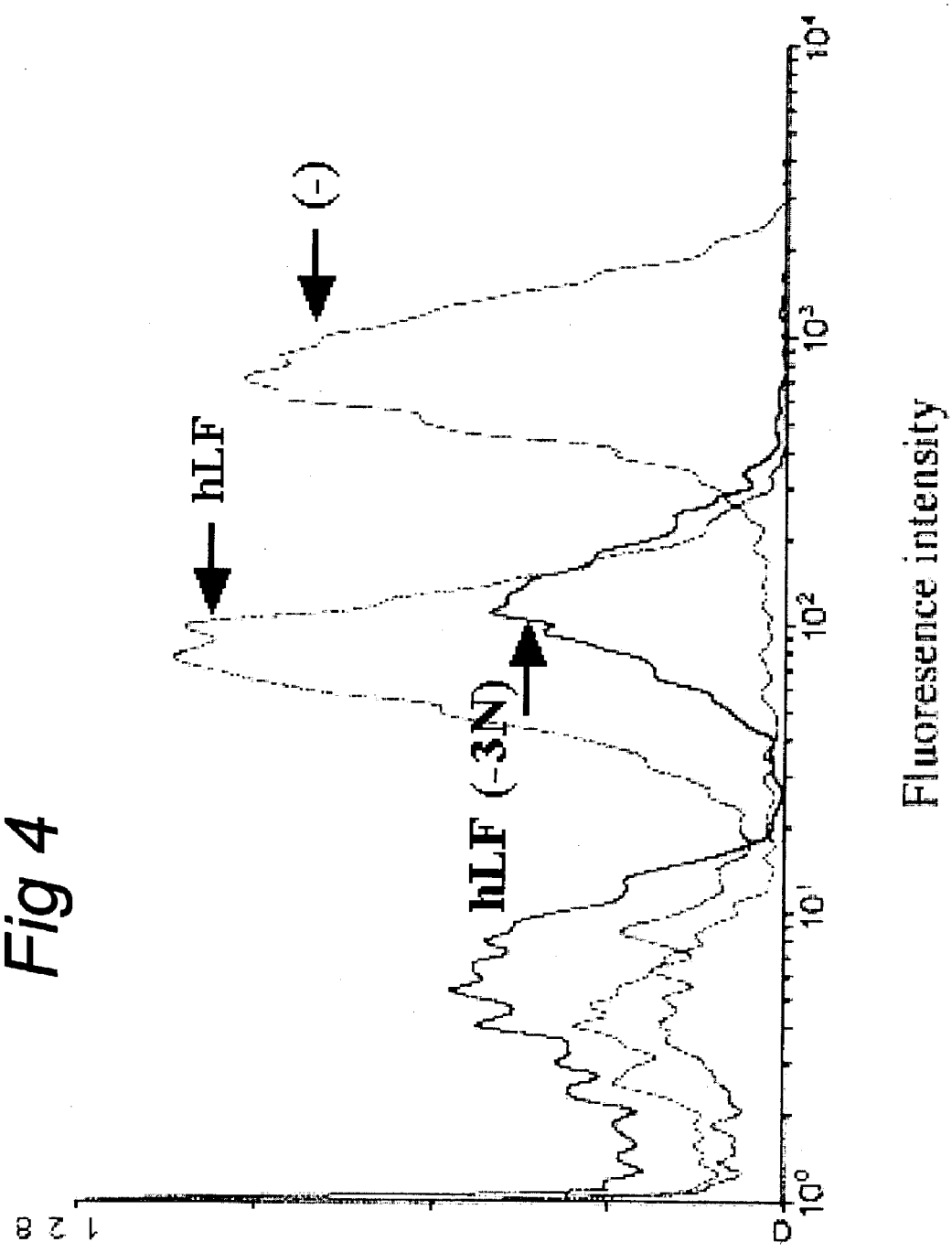
FIG. 4 depicts the effect of natural hLF and hLF$^{-3N}$ on the non-specific esterase activity of *L. monocytogenes*. Approximately 2×10$^6$ CFU of bacteria were initially incubated with 4 µM of natural hLF, hLF$^{-3N}$, or BSA (–) for 2 h at 37° C., and then incubated with 100 µM of 5-sulfofluorescein diacetate in 20% (v/v) ethanol for 20 min at room temperature in the dark. The bacteria were then washed and fluorescence intensity assessed by FACS analysis.

Effect of Natural hLF, hLF$^{-3N}$ and Related Peptides on Membrane Permeability and Intracellular Non-Specific Esterase Activity of Bacteria To gain some insight into the mechanisms underlying the antibacterial activity of hLF as well as related peptides, the effect of these polypeptides on the membrane permeability and the non-specific esterase activity of bacteria was determined according to the procedures described above in Example II. The results revealed that incubation of natural hLF and hLF$^{-3N}$ with *L. monocytogenes* and *E. coli* was not followed by a significant change of the membrane permeability during the period of analysis. i.e., 4 h after addition of these proteins (FIG. 4). Interestingly, natural hLF and hLF-N inhibited the intracellular non-specific esterase activity of *L. monocytogenes*, but not *E. coli* within 1–2 hours after addition of these proteins (FIG. 4). These data indicate that the intracellular effects of hLF (as well as hLF$^{-3N}$) in *L. monocytogenes* are not followed by disruption of the membrane integrity.

In agreement with this possibility, it was found that hLF and hLF$^{-3N}$ at 4° C. had no affect on the number of viable bacteria nor on the non-specific esterase activity, whereas protegrin-1 did. Protegrin-1 kills bacteria through another mechanism, i.e., membrane permeabilization. In contrast to natural hLF and hLF$^{-3N}$ the fragments hLF(1–11) hLF (2–11), hLF(3–11) and hLF(4–11), but not hLF(5–11) and hLF(6–11), influenced the membrane permeability (FIGS. 3A–3C) in a dose- and time-dependent fashion. When studied at concentrations that did not increase the membrane permeability, these peptides did not affect the non-specific esterase activity of bacteria. Finally, dose-effect studies revealed that hLF(1–11) was considerably ($p<0.05$) more efficient than hLF(21–31) in increasing the membrane permeability of bacteria (FIGS. 3A–3C).

EXAMPLE V

Figure 5:
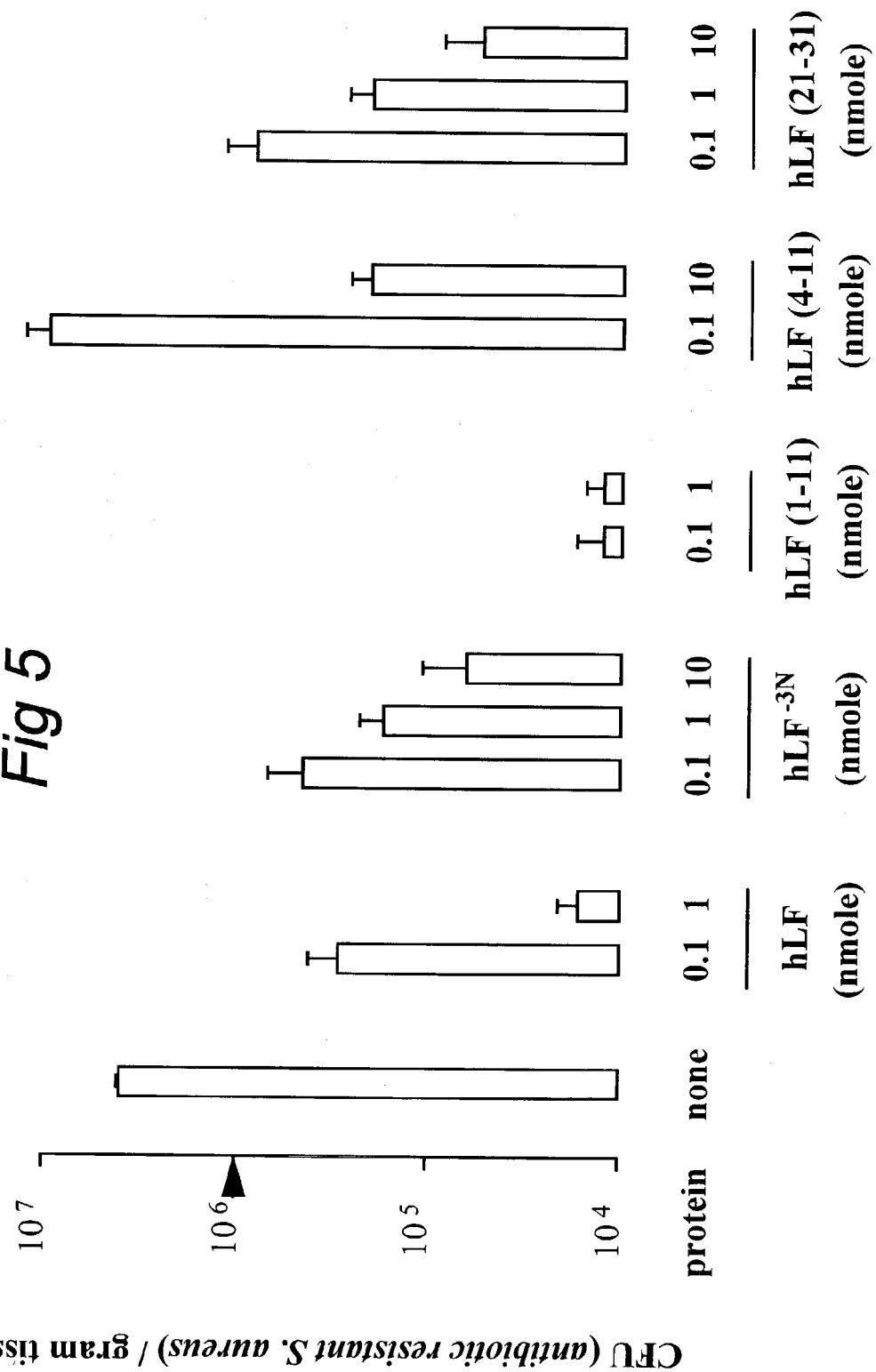
FIG. 5 shows the bactericidal activity of natural hLF, hLF$^{-3N}$ and various related peptides in mice infected with antibiotic resistant *S. aureus*. Mice were intramuscularly infected with approximately 1×10$^6$ CFU of antibiotic resistant *S. aureus* in 0.1 ml of saline. Twenty-four hours thereafter, 0.2 ml of saline containing various amounts (0.1–10 mmole) of natural hLF, hLF$^{-3N}$, hLF(1–11), hLF(4–11) or hLF(21–31) was injected intravenously. At 24 h after injection of radiolabeled peptide, mice were killed by intraperitoneal injection with sodium pentobarbital. Thigh muscle was subsequently removed, weighed, and then homogenized. Serial fold dilutions of these homogenates were pipetted onto plates and the number of CFU determined microbiologically. Values are expressed as mean values (±SD) of the CFU of antibiotic resistant *S. aureus* per gram of thigh muscle (n=3).

Antibacterial Activity of natural hLF, hLF$^{-3N}$ and Related Peptides in Experimental Thigh Muscle Infections The antibacterial activity of hLF and various fragments thereof in treating infections initiated in mice was determined using the methods described in Example II. Within 24 h after injection of natural hLF, hLF$^{-3N}$, hLF(1–11), hLF (4–11) or hLF(21–31) the number of viable bacteria in mice with an infection with antibiotic resistant *S. aureus* was reduced in a dose-dependent fashion, maximum effects were seen with 1 nmole of hLF, 10 nmole of hLF$^{-3N}$, 0.1 nmole of hLF(1–11) and 10 nmole of hLF(21–31) (see FIG. 5). Similar results were found (2–3 log reduction) in mice infected with *K. pneumoniae* (results not shown). The highest amount of hLF(4–11) exerted some antibacterial activity in mice with an infection with antibiotic resistant *S. aureus* (FIG. 5).

Figure 6:
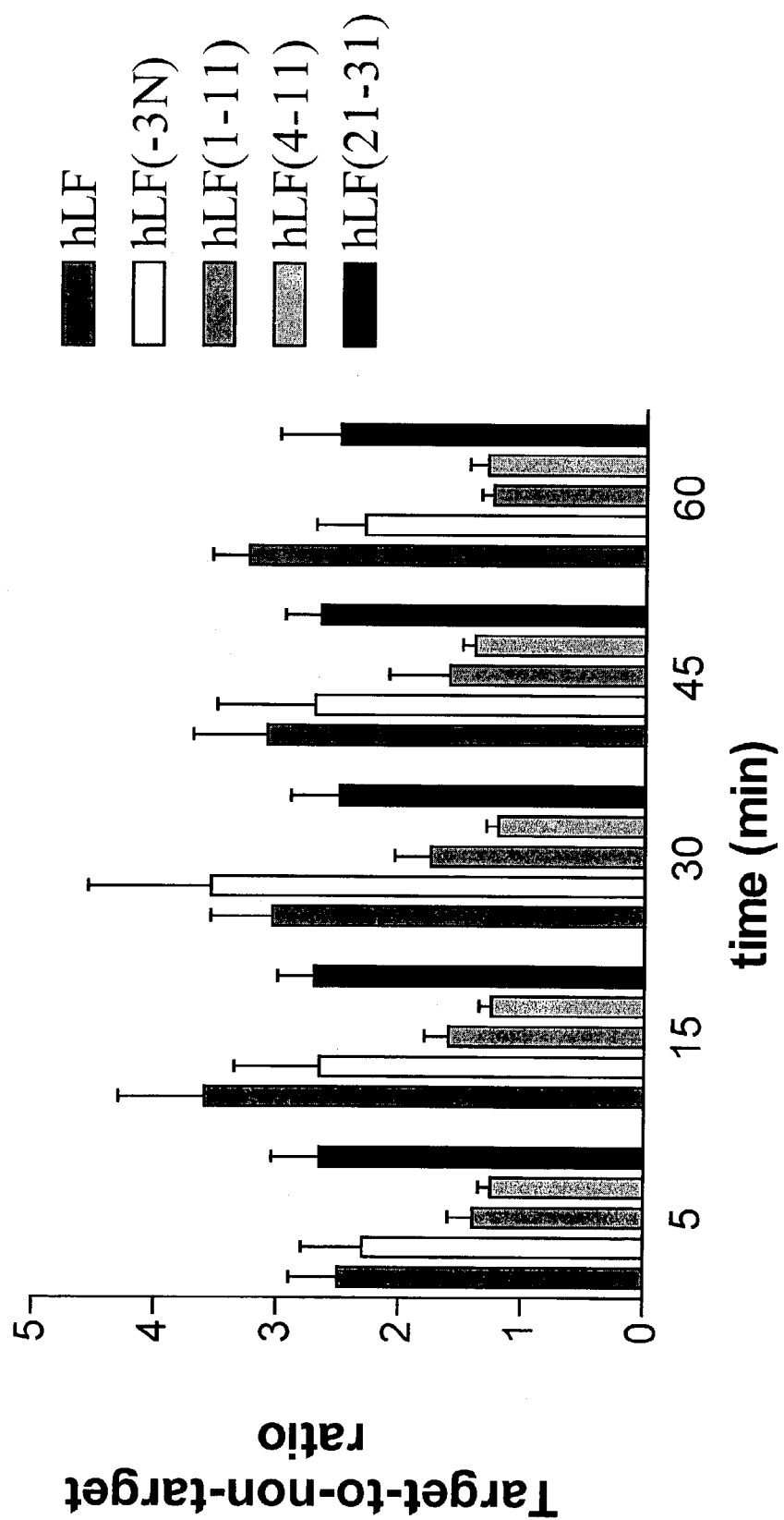
FIG. 6 shows accumulation of $^{99m}$Tc-hLF or related peptides in mice experimentally infected with antibiotic resistant *S. aureus*. Target to non-target ratios for hLF, hLF$^{-3N}$, hLF (1–11), hLF (4–11), or hLF (21–31) in antibiotic resistant *S. aureus* infected mice at various intervals after administration of the radiolabeled protein/peptide. Results are expressed as a mean value (±SD) of at least three mice (p<0.05), compared with $^{99m}$Tc-IgG.

Pharmacological studies revealed that natural hLF, hLF$^{-3N}$ and hLF(1–11), hLF(4–11) and hLF(21–31) were rapidly removed from the circulation of these mice with mean $t_{1/2}$ values of approximately 19 min, 22 min, 9 min, 1 min and 2 min, respectively (n=3) (see FIG. 6 and Table 2). Even within the first min after injection of 1 nmole of radiolabeled natural hLF, hLF$^{-3N}$, hLF(1–11), hLF(4–11) or hLF(21–31) into antibiotic resistant *S. aureus* infected mice, a significant amount of radiolabeled peptide, i.e., approximately 1–1.5% of injected dose (ID), was observed at the site of infection. Moreover, the amount of radiolabeled hLF or related peptide at the site of infection remained constant during the period of analysis. i.e., the first 60 min after injection of the radiolabeled protein or peptide (FIG. 6), indicating that natural hLF, hLF$^{-3N}$ and related peptides quickly reached and accumulated at this site.

EXAMPLE VI

Imaging Microbial Infections

Using $^{99m}$Tc-labeled hLF and related peptides in conjunction with the scintigraphic methods described in the pharmacology section supra, it was possible to detect accumulation of the radio labeled peptides at the site of infection.

hLF and some of the polypeptides of the invention were compared with an established marker of infection/inflammation, (i.e., radiolabeled polyclonal human IgG (23)), for their usefulness in imaging a bacterial infection. The results clearly indicated that radiolabeled hLF and related peptides visualized the infection much faster than radiolabeled IgG. Moreover, hLF(1–11) was also superior to the other peptides and hLF itself.

CONCLUSIONS

The foregoing examples demonstrate that the N-terminal arginines, Arg$^2$ and Arg$^3$, of hLF play an important role in its bactericidal activity. This conclusion is based on the following findings. First, the bactericidal activity of hLF$^{-3N}$, hLF lacking the first three amino acids, was significantly less than that of hLF, both in in vitro studies and in animals having an experimental thigh muscle infection with antibiotic-resistant *S. aureus* and *K. pneuumoniae*. Importantly, the amount of hLF and hLF$^{-3N}$ at the site of infection did not differ, excluding the possibility that the bactericidal activity of these proteins in mice is due to the amount of protein at the site of infection instead of its action. Second, comparison of the bactericidal activities of hLF(1–11) and peptides lacking one or more of the first five residues revealed that Arg$^2$ and Arg$^3$ are important for killing bacteria. In agreement with these in vitro data, hLF(1–11) was found to be much more effective than hLF(4–11) in reducing the number of viable bacteria in antibiotic-resistant *S. aureus*-infected mice.

Interaction of hLF and hLF$^{-3N}$ with bacteria inhibited the non-specific esterase activity of the bacteria without affecting the membrane permeability of the bacteria. While not intending to be held to this particular theory, these observations suggest that hLF is taken up by bacteria where it exerts its effects, such as interaction with ATP (28) and/or mitochondria, as was recently reported for histatin (29). These intracellular actions of hLF could result in disruption of the metabolic activity and subsequently the death of the bacteria. In agreement with this view, it was found that at 4° C. hLF is not able to kill bacteria and to affect the non-specific esterase activity of the bacteria, whereas protegrin-1 can. As for the bactericidal activity of the hLF-derived peptides described herein, the size and tertiary structure of peptides may differ considerably from the same amino acid sequences in natural hLF.

The studies described herein with hLF(21–31) which contains the second cationic domain (i.e., residues 28–31) showed that this polypeptide was considerably less efficient in killing bacteria than hLF(1–11), which suggests that the first cationic domain is significantly more important than the second cationic domain in killing bacteria. In agreement with this conclusion, hLF(21–31) was found to be less effective than hLF(1–11) in reducing the number of viable bacteria in the thigh muscle of mice infected with antibiotic-resistant *S. aureus*. These results are contrary to other reports which emphasize the importance of the second cationic domain in relation to the antibacterial activity of lactoferrin.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby expressly incorporated by reference in their entirety for all purposes to the same extent as if each individual publication patent or patent application were specifically and individually indicated to be so incorporated by reference.

TABLES

TABLE 1

Comparison of the antibacterial activity of natural hLF and hLF$^{3N}$

| Protein | Antibiotic resistant | | CFU of bacteria | |
|---|---|---|---|---|
| | *L. monocytogenes* | *S. aureus* | *K. pneumoniae* | *E. coli* |
| None | $4.4 \pm 1.3 \times 10^6$ | $1.2 \pm 1.5 \times 10^6$ | $2.6 \pm 1.2 \times 10^6$ | $1.1 \pm 1.4 \times 10^6$ |
| BSA | $3.5 \pm 0.6 \times 10^6$ | $1.1 \pm 2.8 \times 10^6$ | $2.1 \pm 0 \times 10^6$ | $1.1 \pm 0.5 \times 10^6$ |
| hLF | $2.4 \pm 0.9 \times 10^{4*,**}$ | $6.9 \pm 2.1 \times 10^{4*,**}$ | $2,1 \pm 0.2 \times 10^{4*,**}$ | $3.0 \pm 0.3 \times 10^6$ |
| hLF$^{3N}$ | $4.8 \pm 2.4 \times 10^{5*}$ | $5.6 \pm 1.9 \times 10^{5*}$ | $6.8 \pm 1.5 \times 10^{5*}$ | $9.5 \pm 8.2 \times 10^5$ |

Approximately $1 \times 10^6$ CFU of *L. monocytogenes*, antibiotic resistant *S. aureus*, *K. pneumoniae*, or *E. coli* were incubated with 4 μM of natural hLF or hLF$^{3N}$, or as control with 8 μM of BSA, in PBS-Tw (pH 6.0) for 3 h at 37° C., washed, and then the number of viable bacteria determined microbiologically. Results are means and SD of 3–5 experiments.
*indicates p < 0.05 for the difference between bactericidal activity of natural hLF or hLF$^{3N}$ versus control (BSA).
**indicates p < 0.05 for the difference between bactericidal activity of hLF$^{3N}$ and natural hLF.

TABLE 2

Uptake of $^{99m}$technetium-labelled natural hLF, hLF-3N, and related peptides by various organs of mice infected with antibiotic resistant *S. aureus*

| Interval | | Protein/peptide (% ID) | | | |
|---|---|---|---|---|---|
| (min) | Organ | HLF | hLF-$^{3N}$ | hLF(1–11) | hLF(21–31) |
| 1 | kidneys | 16 ± 1.9 | 15 ± 1.3 | 18 ± 3.8 | 14 ± 1.1 |
|   | bladder | 15 ± 0.2 | 15 ± 1.7 | 10 ± 1.5 | 20 ± 3.2 |
|   | liver   | 11 ± 1.9 | 17 ± 2.0 | 20 ± 1.6 | 28 ± 1.5 |
| 15 | kidneys | 11 ± 0.1 | 14 ± 1.0 | 21 ± 9.3 | 25 ± 2.5 |
|    | bladder | 31 ± 0.6 | 24 ± 2.1 | 11 ± 7.5 | 34 ± 0.8 |
|    | liver   | 10 ± 2.6 | 15 ± 0.7 | 20 ± 4.9 | 13 ± 7.8 |
| 30 | kidneys | 13 ± 0.8 | 14 ± 1.1 | 17 ± 5.7 | 27 ± 6.6 |
|    | bladder | 37 ± 1.2 | 28 ± 2.8 | 21 ± 5.7 | 37 ± 1.1 |
|    | liver   | 7 ± 1.8  | 17 ± 1.4 | 20 ± 1.6 | 14 ± 11.8 |
| 60 | kidneys | 11 ± 1.7 | 14 ± 0.7 | 14 ± 0.4 | 18 ± 9.9 |
|    | bladder | 40 ± 0.3 | 29 ± 3.4 | 22 ± 5.6 | 38 ± 2.3 |
|    | liver   | 4 ± 0.6  | 10 ± 0.6 | 27 ± 0.6 | 20 ± 6.3 |

Mice infected with antibiotic resistant *S. aureus* were injected with 1 nmole of $^{99m}$technetium-labelled hLF, hLF$^{3N}$, peptides hLF(1–11), hLF (4–11) or hLF(21–31) and at various intervals thereafter the amount of radioactivity in the kidneys, bladder, liver and other organs was determined using a planar gamma camera equipped with a collimator using regions of interest drawn over the various organs. The amounts of radioactivity are expressed as a percentage of the injected dose (% ID). Values are means and SD of three mice.

REFERENCES

1. Nuijens, J. H. Berkel van, P. H. C, and Schanbacher, F. L. 1996. Structure and biological actions of lactoferrin. *J. Mammary Gland Biol. Neoplasia.* 1:285–995.
2. Sanchez, L. Calvo, M., and Brock, J. H. 1992. Biological role of lactoferrin. *Arch Dis. Child.* 67:657–661.
3. Bullen, J. J. 1981. The significance of iron in infection. *Rev. Infect. Dis.* 3:1127–1138.
4. Ellison, R. T., III. 1994. The effects of lactoferrin on Gram-negative bacteria. *Adv. Exp. Med. Biol.* 357:71–90.
5. Bellamy, W., Takase, M., Yamauchi, K., Wakabayashi, H., Kawase, K. et al. 1992. Identification of the bactericidal domain of lactoferrin. *Biochimica Biophysica Acta.* 1121: 130–136.
6. Yamauchi, K., Tomita, M., Giehl, T. J., and Ellison, R. T. 1993. Antibacterial activity of lactoferrin and a pepsin-derived lactoferrin peptide fragment. *Infect Immun.* 61:719–728.
7. Odell, E. W., Sarra. R., Foxworthy, M., Chapple, D. S., and Evans, R. W. 1996. Antibacterial activity of peptides homologous to a loop region in human lactoferrin. *FEBS Letters* 382:175–178.
8. Tomita, M., Bellamy, W., Takase, M., Yamauchi, K., Wakabayashi. H. et al. 1991. Potent antibacterial peptides generated by pepsin digestion of bovine lactoferrin. *J. Dairy Sci.* 74:4137–4142.
9. Hoek, K. S., Milne, J. M., Grieve, P. A., Dionysius, D. A., and Smith, R. 1997. Antibacterial activity of bovine lactoferrin-derived peptides. *Antimicrob. Agents Chemother.* 41:54–59.
10. Dionysius, D. A., and Milne J. M. 1997. Antibacterial peptides of bovine lactoferrin: purification and characterization. *J. Dairy Sci.* 80:667–674.
11. Martin, E., Ganz, T., and Lehrer, R. I. 1995. Defensins and other endogenous peptide antibiotics of vertebrates. *J. Leucokyte. Biol.* 58:128–137.
12. Chapple, D. S. Mason, D. J., Joannou, C. L., Odell, E. W., Gant, V. et al. 1998. Structure-function relationship of antibacterial synthetic peptides homologous to a helical surface region on human lactoferrin against *Escherichia coli* serotype O111. *Infect. Immun.* 66:2434–2440.
13. Mann, D. M., Romm, E., and Migliorini, M. 1994. Delineation of the glycosaminoglycan-binding site in the human inflammatory response protein lactoferrin. *J. Biol. Chem.* 269:23661–23667.
14. Berkel van, P. H. C., Geerts, M. E. J. Veen van, H. A., Mericskay, M. Boer de, H. A. et al. 1997. N-terminal stretch Arg$^2$, Arg$^3$, Arg$^4$, and Arg$^5$ of human lactoferrin is essential for binding to heparin, bacterial lipopolysaccharide, human lysozyme and DNA. *Biochem. J.* 328:145–151.
15. Zhang G. H., Mann, D. M. and Tsai, C. M. 1999. Neutralization of endotoxin in vitro and in vivo by a human lactoferrin-derived peptide. *Infect. Immun.* 67(3): 1353–1358.
16. Wu, H. D. Monroe, M., and Church, F. C. 1995. Characterization of the glycosaminoglycan-binding region of lactoferrin. *Arch. Biochem. Biophys* 317:85–92.
17. Elass-Rochard E., Roseanu, A., Legrand, D. Trif, M., Salmon, V. et al. 1995. Lactoferrin-lipopolysaccharide interactions: involvement of the 28–34 loop region of human lactoferrin in the high affinity binding of *Escherichia coli* O55B5 lipopolysaccharide. *Biochem. J.* 312: 839–84.
18. Legrand, D., Berkel van, P. H. Salmon, V., Veen van, H. A., Slomianny. M. C. et al. 1997. The N-terminal Arg$^2$, Arg$^3$, Arg$^4$ of human lactoferrin interact with sulphated molecules but not with the receptor present on Jurkat human lymphoblastic T-cells. *Biochem. J.* 327:841–846.
19. Koster de, H. S., Amons, R., Benckchuijsen, W. E., Feijlbrief, M., Schellekens, G. A. et al. 1995. The use of dedicated peptide libraries permits the discovery of high affinity binding peptides. *J. Immunol Meth.* 197:179–188.
20. Mason, D. J., Dybowski, R., Larrick, J. W., and Gant, V. A. 1997. Antimicrobial action of rabbit leukocyte CAP18$_{106-137}$. *Antimicrob. Agents. Chemother.* 41:624–629.
21. Tsuji, T., Kawasaki, Y., Takeshima, S. Sekiya, T. and Tanaka, S. 1995. A new fluorescence staining assay for visualizing living microorganisms in soil. *Appl. Environ. Microbiol.* 61:3415–3421.
22. Pauwels, E. K. J. Welling, M. M., Feitsma, R. I. J., Atsma, D. E., and Nieuwenhuizen, W. 1993. The labeling of proteins and LDL with $^{99m}$Tc: a new direct method employing KBH$_4$ and stannous chloride. *Nucl. Med. Biol.* 20:8925–833.
23. Welling, M. M., Hiemstra, P. S. Barselaar van den, M. T. Annema-Paulusma. A. Nibbering, P. H. et al. 1998. Antibacterial activity of human neutrophil defensins in experimental infections in mice is accompanied by increased leukocyte accumulation. *J. Clin. Invest.* 8:1583–1590.
24. Hutchens, T. W., Henry, J. F., and Yip, T. T. 1991. Structurally intact (78-kDa) forms of maternal lactoferrin purified from urine of preterm infants fed human milk: identification of a trypsin-like proteolytic cleavage event in vivo that does not result in fragment dissociation. *Proc. Natl. Acad. Sci. USA.* 15:2994–9998.
25. Schryvers, A. B., Bonnah, R., Wong, H., and Retzer, M. 1998. Bacterial lactoferrin receptors. *Adv. Exp. Med. Biol.* 443:123–133.
26. Erdei, J., Forsgren, A., and Naidu, A. S. 1994. Lactoferrin binds to porins OmpI and OmpC in *Escherichia coli Infect. Immun.* 62:1236–1240.

27. Welling, M., Annema-Paulusma, A. Pauwels, E. K. J., and Nibbering, P. H. 1999. $^{99m}$Technetium labelled antimicrobial peptides that discriminate between bacterial infections and sterile inflammations. *Eur. J. Nucl. Med.* In press.
28. Semenov, D. V. Kanyshkova, T. G., Akimzhanov, A. M., Buneva, V. N. and Nevinsky, G. A. 1998. Interaction of human milk lactoferrin with ATP. *Biochem. (Mosc)* 63:944–951.
29. Helmershorst E. J., Breeuwe, P., Hof van het, W., Walgreen-Weterings, W., Oomen, L. C. J. M. et al. 1999. The cellular target of histatin 5 on *Candida Albicans* is the energized mitochondrion *J. Biol. Chem.* 274:7286–7291.
30. Ward, P. P., Piddington, C. S., Cunningham, G. A., Zhou, X., Wyatt, R. D. et al. 1995. A system for production of commercial quantities of human lactoferrin: a broad spectrum natural antibiotic. *Bio Technol.* 13:498–503.
31. Ellison, R. T., Giehl, T. J., and LaForce, M. 1988. Damage of the outer membrane of enteric Gram-negative bacteria by lactoferrin and transferrin. *Infect. Immun.* 56:2774–2781.
32. Iyer, S., and Lonnerdal, B. (1993) *Eur. J. Clin. Nutr.* 47, 232–241.
33. Huettinger, M., Retzek, H., Hermann, M., and Goldenberg, H. (1992) *J. Biol Chem.* 67 18551–18557.
34. Willnow, T. E., Goldstein, J. L., Orth, K., Brown, M. S., and Herz, J. (1992) *J. Biol. Chem.* 267, 26172–26180.
35. Bartal, L., Padeh, S., and Passwell, J. L. (1987) *Pediatr. Res.* 21, 54–57.
36. Zucali, J. R. Broxmeyer, H. E., Levy, D., and Morse, C. (1989) *Blood* 74, 1531–1536.
37. Crouch, S. P. M. Slater, K. J., and Fletcher, J. (1992) *Blood* 80, 35–240.

The invention claimed is:

1. An isolated polypeptide comprising at least 6 contiguous amino acids starting at residue 1 from human lactoferrin protein (SEQ ID NO:1), wherein the polypeptide has antimicrobial activity, and provided the polypeptide has fewer than 18 contiguous amino acids from SEQ ID NO:1, and the polypeptide is not hLF1–11.

2. The polypeptide of claim 1, wherein said polypeptide comprises at least 7 contiguous amino acids of SEQ ID NO:1.

3. The polypeptide of claim 1, wherein said polypeptide comprises at least 8 contiguous amino acids of SEQ ID NO:1.

4. The polypeptide of claim 1, wherein the amino acid residues of said polypeptide consist of residues 1 to 9 of SEQ ID NO:1.

5. An isolated polypeptide comprising at least 6 contiguous amino acids starting at residue 2 from the human lactoferrin protein (SEQ ID NO:1), wherein the polypeptide has antimicrobial activity, and provided the polypeptide has not more than 26 contiguous amino acids from SEQ ID NO:1.

6. The polypeptide of claim 5, wherein the amino acid residues of said polypeptide consist of residues 2 to 11 of SEQ ID NO:1.

7. An isolated polypeptide comprising at least 6 contiguous amino acids starting at residue 3 from human lactoferrin protein (SEQ ID NO:1), wherein the polypeptide has antimicrobial activity, and provided the polypeptide has not more than 25 contiguous amino acids from SEQ ID NO:1.

8. The polypeptide of claim 7, wherein the amino acid residues of said polypeptide consist of residues 3 to 11 of SEQ ID NO:1.

9. A pharmaceutical composition comprising a polypeptide and a pharmaceutically acceptable excipient, wherein said polypeptide is selected from the group consisting of:
   (a) a polypeptide comprising at least 6 contiguous amino acids starting at residue 1 from human lactoferrin protein (SEQ ID NO:1), wherein the polypeptide has antimicrobial activity, and provided the polypeptide has fewer than 18 contiguous amino acids from SEQ ID NO:1, and the polypeptide is not hLF1–11;
   (b) a polypeptide comprising at least 6 contiguous amino acids starting at residue 2 from human lactoferrin protein (SEQ ID NO:1), wherein the polypeptide has antimicrobial activity, and provided the polypeptide has not more than 26 contiguous amino acids from SEQ ID NO:1; and
   (c) a polypeptide comprising at least 6 contiguous amino acids starting at residue 3 from human lactoferrin protein (SEQ ID NO:1), wherein the polypeptide has antimicrobial activity, and provided the polypeptide has not more than 25 contiguous amino acids from SEQ ID NO:1.

10. The pharmaceutical composition of claim 9, wherein said polypeptide is at least 7 amino acids in length.

11. The pharmaceutical composition of claim 9, wherein said polypeptide is 11 amino acids in length.

12. The pharmaceutical composition of claim 9, wherein said polypeptide is a polypeptide comprising at least 6 starting at residue 2 from human lactoferrin protein (SEQ ID NO:1), wherein the polypeptide has antimicrobial activity, and provided the polypeptide has not more than 26 contiguous amino acids from SEQ ID NO:1.

13. The pharmaceutical composition of claim 12, wherein the amino acid residues of said polypeptide consist of residues 2 to 11 of SEQ ID NO:1.

14. The pharmaceutical composition of claim 9, wherein said polypeptide is a polypeptide comprising at least 6 contiguous amino acids starting at residue 3 from human lactoferrin protein (SEQ ID NO:1), wherein the polypeptide has antimicrobial activity, and provided the polypeptide has not more than 25 contiguous amino acids from SEQ ID NO:1.

15. The pharmaceutical composition of claim 14, wherein the amino acid residues of said polypeptide consist of residues 3 to 11 of SEQ ID NO:1.

16. A method for treating a patient infected with a microbe, comprising administering to said patient a therapeutic dose of a polypeptide selected from the group consisting of:
   (a) a polypeptide comprising at least 6 contiguous amino acids starting at residue 1 from human lactoferrin protein (SEQ ID NO:1), wherein the polypeptide has antimicrobial activity, and provided the polypeptide has not more than 27 contiguous amino acids from SEQ ID NO:1;
   (b) a polypeptide comprising at least 6 contiguous amino acids starting at residue 2 from human lactoferrin protein (SEQ ID NO:1), wherein the polypeptide has antimicrobial activity, and provided the polypeptide has not more than 26 contiguous amino acids from SEQ ID NO:1; and
   (c) a polypeptide comprising at least 6 contiguous amino acids starting at residue 3 from human lactoferrin protein (SEQ ID NO:1), wherein the polypeptide has antimicrobial activity, and provided the polypeptide has not more than 25 contiguous amino acids from SEQ ID NO:1.

17. The method of claim 16, wherein said microbe is a Gram-negative bacterium.

18. The method of claim 16, wherein said microbe is a Gram-positive bacterium.

19. The method of claim 16, wherein said microbe is a bacterium selected from the group consisting of *Listeria*, *Staphylococcus*, *Klebsiella* and *Escherichia*.

20. The method of claim 19, wherein said bacterium is selected from the group consisting of *Listeria monocytogenes*, *Staphylococcus aureus*, and *Escherichia coli*.

21. The method of claim 19, wherein said dose is administered using oral, intravenous, intraperitoneal, subcutaneous, intramuscular, topical or intranasal methods.

22. A method for treating a patient infected with a microbe, comprising administering to said patient a therapeutic dose of a polypeptide of claim 5.

23. A method for treating a patient infected with a microbe, comprising administering to said patient a therapeutic dose of a polypeptide of claim 7.

24. A method for treating a patient infected with a microbe, comprising administering to said patient a therapeutic dose of a pharmaceutical composition of claim 9.

25. A method for treating a patient infected with a microbe, comprising administering to said patient a therapeutic dose of a pharmaceutical composition of claim 12.

26. A method for treating a patient infected with a microbe, comprising administering to said patient a therapeutic dose of a pharmaceutical composition of claim 14.

27. A method for altering the permeability of a bacterial cell membrane, comprising contacting a bacterial cell with a polypeptide having antimicrobial activity selected from the group consisting of:
   (a) a polypeptide comprising at least 6 contiguous amino acids starting at residue 1 from human lactoferrin protein (SEQ ID NO:1), wherein the polypeptide has antimicrobial activity, and provided the polypeptide has not more than 27 contiguous amino acids from SEQ ID NO:1;

(b) a polypeptide comprising at least 6 contiguous amino acids starting at residue 2 from human lactoferrin protein (SEQ ID NO:1), wherein the polypeptide has antimicrobial activity, and provided the polypeptide has not more than 26 contiguous amino acids from SEQ ID NO:1; and (c) a polypeptide comprising at least 6 contiguous amino acids starting at residue 3 from human lactoferrin protein (SEQ ID NO:1), wherein the polypeptide has antimicrobial activity, and provided the polypeptide has not more than 25 contiguous amino acids from SEQ ID NO:1.

28. The method of claim 27, wherein said bacteria cell is selected from the group consisting of *Listeria, Staphylococcus, Klebsiella* and *Escherichia.*

29. A method for altering the permeability of a bacterial cell membrane, comprising contacting a bacterial cell membrane with a polypeptide of claim 5.

30. A method for altering the permeability of a bacterial cell membrane, comprising contacting a bacterial cell membrane with a polypeptide of claim 7.

31. The isolated polypeptide of claim 5, wherein the polypeptide comprises at least 8 contiguous amino acids from the N-terminal segment.

32. The isolated polypeptide of claim 7, wherein the polypeptide comprises at least 7 contiguous amino acids from the N-terminal segment.

33. The pharmaceutical composition of claim 9, wherein the polypeptide has an amino acid sequence consisting of at least 8 but not more than 26 contiguous amino acids from the N-terminal segment of human lactoferrin, wherein the N-terminus of said polypeptide is residue 2.

34. The pharmaceutical composition of claim 9, wherein the polypeptide has an amino acid sequence consisting of at least 7 but not more than 25 contiguous amino acids from the N-terminal segment of human lactoferrin, wherein the N-terminus of said polypeptide is residue 3.

35. The method of claim 16, wherein the polypeptide has an amino acid sequence consisting of at least 9 but not more than 27 contiguous amino acids from the N-terminal segment of human lactoferrin protein (SEQ ID NO:1), wherein the N-terminus of said polypeptide is residue 1.

36. The method of claim 16, wherein the polypeptide has an amino acid sequence consisting of at least 8 but not more than 26 contiguous amino acids from the N-terminal segment of human lactoferrin protein, wherein the N-terminus of said polypeptide is residue 2.

37. The method of claim 16, wherein the polypeptide has an amino acid sequence consisting of at least 7 but not more than 25 contiguous amino acids from the N-terminal segment of human lactoferrin protein, wherein the N-terminus of said polypeptide is residue 3.

38. The method of claim 27, wherein the polypeptide has an amino acid sequence consisting of at least 9 but not more than 27 contiguous amino acids from the N-terminal segment of human lactoferrin protein (SEQ ID NO:1), wherein the N-terminus of said polypeptide is residue 1.

39. The method of claim 27, wherein the polypeptide has an amino acid sequence consisting of at least 8 but not more than 26 contiguous amino acids from the N-terminal segment of human lactoferrin protein, wherein the N-terminus of said polypeptide is residue 2.

40. The method of claim 27, wherein the polypeptide has an amino acid sequence consisting of at least 7 but not more than 25 contiguous amino acids from the N-terminal segment of human lactoferrin protein, wherein the N-terminus of said polypeptide is residue 3.

41. The method of claim 16, wherein the amino acid residues of the polypeptide consists of residues 1–11 of SEQ ID NO:1.

\* \* \* \* \*

SEQUENCE LISTING

```
<160> NUMBER OF SEQ ID NOS: 6

<210> SEQ ID NO 1
<211> LENGTH: 692
<212> TYPE: PRT
<213> ORGANISM: Homo sapiens

<400> SEQUENCE: 1

Gly Arg Arg Arg Ser Val Gln Trp Cys Ala Val Ser Gln Pro Glu
 1               5                  10                  15

Ala Thr Lys Cys Phe Gln Trp Gln Arg Asn Met Arg Lys Val Arg Gly
                20                  25                  30

Pro Pro Val Ser Cys Ile Lys Arg Asp Ser Pro Ile Gln Cys Ile Gln
            35                  40                  45

Ala Ile Ala Glu Asn Arg Ala Asp Ala Val Thr Leu Asp Gly Gly Phe
        50                  55                  60

Ile Tyr Glu Ala Gly Leu Ala Pro Tyr Lys Leu Arg Pro Val Ala Ala
 65                  70                  75                  80

Glu Val Tyr Gly Thr Glu Arg Gln Pro Arg Thr His Tyr Tyr Ala Val
                85                  90                  95

Ala Val Val Lys Lys Gly Gly Ser Phe Gln Leu Asn Glu Leu Gln Gly
            100                 105                 110

Leu Lys Ser Cys His Thr Gly Leu Arg Arg Thr Ala Gly Trp Asn Val
        115                 120                 125

Pro Ile Gly Thr Leu Arg Pro Phe Leu Asn Trp Thr Gly Pro Pro Glu
    130                 135                 140

Pro Ile Glu Ala Ala Val Ala Arg Phe Phe Ser Ala Ser Cys Val Pro
145                 150                 155                 160

Gly Ala Asp Lys Gly Gln Phe Pro Asn Leu Cys Arg Leu Cys Ala Gly
                165                 170                 175

Thr Gly Glu Asn Lys Cys Ala Phe Ser Ser Gln Glu Pro Tyr Phe Ser
            180                 185                 190

Tyr Ser Gly Ala Phe Lys Cys Leu Arg Asp Gly Ala Gly Asp Val Ala
        195                 200                 205

Phe Ile Arg Glu Ser Thr Val Phe Glu Asp Leu Ser Asp Glu Ala Glu
    210                 215                 220

Arg Asp Glu Tyr Glu Leu Leu Cys Pro Asp Asn Thr Arg Lys Pro Val
225                 230                 235                 240
```

-continued

Asp Lys Phe Lys Asp Cys His Leu Ala Arg Val Pro Ser His Ala Val
            245                 250                 255

Val Ala Arg Ser Val Asn Gly Lys Glu Asp Ala Ile Trp Asn Leu Leu
            260                 265                 270

Arg Gln Ala Gln Glu Lys Phe Gly Lys Asp Lys Ser Pro Lys Phe Gln
        275                 280                 285

Leu Phe Gly Ser Pro Ser Gly Gln Lys Asp Leu Leu Phe Lys Asp Ser
    290                 295                 300

Ala Ile Gly Phe Ser Arg Val Pro Pro Arg Ile Asp Ser Gly Leu Tyr
305                 310                 315                 320

Leu Gly Ser Gly Tyr Phe Thr Ala Ile Gln Asn Leu Arg Lys Ser Glu
                325                 330                 335

Glu Glu Val Ala Ala Arg Arg Ala Arg Val Val Trp Cys Ala Val Gly
            340                 345                 350

Glu Gln Glu Leu Arg Lys Cys Asn Gln Trp Ser Gly Leu Ser Glu Gly
        355                 360                 365

Ser Val Thr Cys Ser Ser Ala Ser Thr Thr Glu Asp Cys Ile Ala Leu
    370                 375                 380

Val Leu Lys Gly Glu Ala Asp Ala Met Ser Leu Asp Gly Gly Tyr Val
385                 390                 395                 400

Tyr Thr Ala Gly Lys Cys Gly Leu Val Pro Val Leu Ala Glu Asn Tyr
                405                 410                 415

Lys Ser Gln Gln Ser Ser Asp Pro Asp Pro Asn Cys Val Asp Arg Pro
            420                 425                 430

Val Glu Gly Tyr Leu Ala Val Ala Val Val Arg Arg Ser Asp Thr Ser
        435                 440                 445

Leu Thr Trp Asn Ser Val Lys Gly Lys Lys Ser Cys His Thr Ala Val
    450                 455                 460

Asp Arg Thr Ala Gly Trp Asn Ile Pro Met Gly Leu Leu Phe Asn Gln
465                 470                 475                 480

Thr Gly Ser Cys Lys Phe Asp Glu Tyr Phe Ser Gln Ser Cys Ala Pro
                485                 490                 495

Gly Ser Asp Pro Arg Ser Asn Leu Cys Ala Leu Cys Ile Gly Asp Glu
            500                 505                 510

Gln Gly Glu Asn Lys Cys Val Pro Asn Ser Asn Glu Arg Tyr Tyr Gly
        515                 520                 525

Tyr Thr Gly Ala Phe Arg Cys Leu Ala Glu Asn Ala Gly Asp Val Ala
    530                 535                 540

Phe Val Lys Asp Val Thr Val Leu Gln Asn Thr Asp Gly Asn Asn Asn
545                 550                 555                 560

Glu Ala Trp Ala Lys Asp Leu Lys Leu Ala Asp Phe Ala Leu Leu Cys
                565                 570                 575

Leu Asp Gly Lys Arg Lys Pro Val Thr Glu Ala Arg Ser Cys His Leu
            580                 585                 590

Ala Met Ala Pro Asn His Ala Val Val Ser Arg Met Asp Lys Val Glu
        595                 600                 605

Arg Leu Lys Gln Val Leu Leu His Gln Gln Ala Lys Phe Gly Arg Asn
    610                 615                 620

Gly Ser Asp Cys Pro Asp Lys Phe Cys Leu Phe Gln Ser Glu Thr Lys
625                 630                 635                 640

Asn Leu Leu Phe Asn Asp Asn Thr Glu Cys Leu Ala Arg Leu His Gly
                645                 650                 655

Lys Thr Thr Tyr Glu Lys Tyr Leu Gly Pro Gln Tyr Val Ala Gly Ile

```
            660                 665                 670
Thr Asn Leu Lys Lys Cys Ser Thr Ser Pro Leu Leu Glu Ala Cys Glu
        675                 680                 685

Phe Leu Arg Lys
    690
```

<210> SEQ ID NO 2
<211> LENGTH: 11
<212> TYPE: PRT
<213> ORGANISM: Homo sapiens

<400> SEQUENCE: 2

```
Gly Arg Arg Arg Arg Ser Val Gln Trp Cys Ala
  1               5                  10
```

<210> SEQ ID NO 3
<211> LENGTH: 27
<212> TYPE: PRT
<213> ORGANISM: Homo sapiens

<400> SEQUENCE: 3

```
Gly Arg Arg Arg Arg Ser Val Gln Trp Cys Ala Val Ser Gln Pro Glu
  1               5                  10                  15

Ala Thr Lys Cys Phe Gln Trp Gln Arg Asn Met
             20                  25
```

<210> SEQ ID NO 4
<211> LENGTH: 11
<212> TYPE: PRT
<213> ORGANISM: Homo sapiens

<400> SEQUENCE: 4

```
Phe Gln Trp Gln Arg Asn Met Arg Lys Val Arg
  1               5                  10
```

<210> SEQ ID NO 5
<211> LENGTH: 19
<212> TYPE: PRT
<213> ORGANISM: Homo sapiens

<400> SEQUENCE: 5

```
Arg Gly Gly Arg Leu Cys Tyr Cys Arg Arg Arg Phe Cys Val Cys Val
  1               5                  10                  15

Val Gly Arg
```

<210> SEQ ID NO 6
<211> LENGTH: 19
<212> TYPE: PRT
<213> ORGANISM: Human immunodeficiency virus type 1

<400> SEQUENCE: 6

```
Arg Pro Val Val Ser Thr Gln Leu Leu Asn Gly Ser Leu Ala Glu Glu
  1               5                  10                  15

Glu Val Val
```